US010549016B2

(12) United States Patent
Bushko et al.

(10) Patent No.: US 10,549,016 B2
(45) Date of Patent: Feb. 4, 2020

(54) BLOCKAGE DETECTION IN REDUCED PRESSURE THERAPY

(71) Applicant: Smith & Nephew, Inc., Memphis, TN (US)

(72) Inventors: Justin A. Bushko, Clearwater, FL (US); William Joseph Jaecklein, Saint Petersburg, FL (US); Felix C. Quintanar, Hull (GB); Christopher Karl Walter Rouseff, Saint Petersburg, FL (US)

(73) Assignee: Smith & Nephew, Inc., Memphis, TN (US)

(*) Notice: Subject to any disclaimer, the term of this patent is extended or adjusted under 35 U.S.C. 154(b) by 398 days.

(21) Appl. No.: 15/540,988

(22) PCT Filed: Nov. 18, 2015

(86) PCT No.: PCT/US2015/061430
§ 371 (c)(1),
(2) Date: Jun. 29, 2017

(87) PCT Pub. No.: WO2016/109048
PCT Pub. Date: Jul. 7, 2016

(65) Prior Publication Data
US 2017/0354768 A1    Dec. 14, 2017

Related U.S. Application Data

(60) Provisional application No. 62/098,130, filed on Dec. 30, 2014, provisional application No. 62/211,430, filed on Aug. 28, 2015.

(51) Int. Cl.
*A61M 1/00* (2006.01)

(52) U.S. Cl.
CPC ........ *A61M 1/0035* (2014.02); *A61M 1/0088* (2013.01); *A61M 1/0025* (2014.02);
(Continued)

(58) Field of Classification Search
CPC .............. A61M 1/0025; A61M 1/0031; A61M 1/0035; A61M 1/0088; A61M 1/0094;
(Continued)

(56) References Cited

U.S. PATENT DOCUMENTS 4,832,299 A    5/1989  Gorton et al.
5,219,428 A    6/1993  Stern
(Continued)

FOREIGN PATENT DOCUMENTS

CA    2 819 475    6/2012
CN    201379831    1/2010
(Continued)

OTHER PUBLICATIONS

International Preliminary Report on Patentability and Written Opinion, re PCT/US2014/026692, dated Sep. 24, 2015.
(Continued)

*Primary Examiner* — Benjamin J Klein
(74) *Attorney, Agent, or Firm* — Knobbe, Martens, Olson & Bear, LLP

(57) ABSTRACT

Embodiments of negative pressure wound therapy systems and methods for operating the systems are disclosed. In some embodiments, a system includes a pump assembly and a wound dressing configured to be positioned over a wound. The pump assembly and the wound dressing can be fluidically connected to facilitate delivery of negative pressure to a wound via a fluid flow path. The system can be configured to efficiently deliver negative pressure and to detect and indicate presence of conditions, such as a blockage in a fluid (Continued)

flow path. Monitoring of the conditions can be performed by detecting a level of activity of a pump of the pump assembly.

26 Claims, 17 Drawing Sheets

(52) U.S. Cl.
CPC ..... *A61M 2205/15* (2013.01); *A61M 2205/18* (2013.01); *A61M 2205/3331* (2013.01); *A61M 2205/3365* (2013.01); *A61M 2205/581* (2013.01)

(58) Field of Classification Search
CPC .......... A61M 2205/15; A61M 2205/18; A61M 2205/3331; A61M 2205/3365; A61M 2205/581; A61F 13/00068; A61F 13/0216
See application file for complete search history.

(56) References Cited

U.S. PATENT DOCUMENTS

| | | |
|---|---|---|
| 5,449,347 A | 9/1995 | Preen et al. |
| 5,466,229 A | 11/1995 | Elson |
| 5,582,601 A | 12/1996 | Wortrich et al. |
| 5,584,824 A | 12/1996 | Gillette et al. |
| 5,622,429 A | 4/1997 | Heinze |
| 5,656,027 A | 8/1997 | Ellingboe |
| 5,669,892 A | 9/1997 | Keogh et al. |
| 5,693,013 A | 12/1997 | Geuder |
| 6,241,739 B1 | 6/2001 | Waldron |
| 6,572,530 B1 | 6/2003 | Araki et al. |
| 6,605,032 B2 | 8/2003 | Benkowski et al. |
| 7,004,915 B2 | 2/2006 | Boynton et al. |
| 7,128,735 B2 | 10/2006 | Weston |
| 7,361,184 B2 | 4/2008 | Joshi |
| 7,553,306 B1 | 6/2009 | Hunt et al. |
| 7,611,500 B1 | 11/2009 | Lina et al. |
| 7,615,036 B2 | 11/2009 | Joshi et al. |
| 7,670,323 B2 | 3/2010 | Hunt et al. |
| 7,723,560 B2 | 5/2010 | Lockwood et al. |
| 7,776,028 B2 | 8/2010 | Miller et al. |
| 7,779,625 B2 | 8/2010 | Joshi et al. |
| 7,846,141 B2 | 12/2010 | Weston |
| 7,857,806 B2 | 12/2010 | Karpowicz et al. |
| 7,927,319 B2 | 4/2011 | Lawhorn |
| 8,061,360 B2 | 11/2011 | Locke et al. |
| 8,246,607 B2 | 8/2012 | Karpowicz et al. |
| 8,257,328 B2 | 9/2012 | Augustine et al. |
| 8,267,918 B2 | 9/2012 | Johnson et al. |
| 8,294,586 B2 | 10/2012 | Pidgeon et al. |
| 8,308,714 B2 | 11/2012 | Weston et al. |
| 8,494,349 B2 | 7/2013 | Gordon |
| 8,540,688 B2 | 9/2013 | Eckstein et al. |
| 8,617,129 B2 | 12/2013 | Hartwell |
| 8,622,981 B2 | 1/2014 | Hartwell et al. |
| 8,652,111 B2 | 2/2014 | Pratt et al. |
| 8,668,677 B2 | 3/2014 | Eckstein et al. |
| 8,694,600 B2 | 4/2014 | Gaines et al. |
| 8,747,376 B2 | 6/2014 | Locke et al. |
| 8,771,259 B2 | 7/2014 | Karpowicz et al. |
| 8,801,685 B2 | 8/2014 | Armstrong et al. |
| 8,814,841 B2 | 8/2014 | Hartwell |
| 8,814,842 B2 | 8/2014 | Coulthard et al. |
| 8,827,983 B2 | 9/2014 | Braga et al. |
| 8,843,327 B2 | 9/2014 | Vernon-Harcourt et al. |
| 8,845,603 B2 | 9/2014 | Middleton et al. |
| 8,858,517 B2 | 10/2014 | Pan et al. |
| 8,945,074 B2 | 2/2015 | Buan et al. |
| 8,974,429 B2 | 3/2015 | Gordon et al. |
| 9,017,286 B2 | 4/2015 | Kamen et al. |
| 9,084,845 B2 | 7/2015 | Adie et al. |
| 9,408,954 B2 | 8/2016 | Gordon et al. |
| 9,636,440 B2 | 5/2017 | Weston et al. |
| 2001/0013822 A1 | 8/2001 | Nazarian et al. |
| 2001/0031944 A1 | 10/2001 | Peterson et al. |
| 2002/0026160 A1 | 2/2002 | Takahashi et al. |
| 2002/0082568 A1 | 6/2002 | Yam |
| 2002/0161317 A1 | 10/2002 | Risk et al. |
| 2002/0193679 A1 | 12/2002 | Malave et al. |
| 2003/0028175 A1 | 2/2003 | D'Antonio |
| 2003/0093041 A1 | 5/2003 | Risk, Jr. et al. |
| 2003/0164600 A1 | 9/2003 | Dunn et al. |
| 2004/0039255 A1 | 2/2004 | Simonsen et al. |
| 2004/0054338 A1 | 3/2004 | Bybordi et al. |
| 2004/0059284 A1 | 3/2004 | Nash et al. |
| 2004/0064132 A1 | 4/2004 | Boehringer et al. |
| 2004/0102743 A1 | 5/2004 | Walker |
| 2004/0171982 A1 | 9/2004 | Danchin |
| 2004/0181314 A1 | 9/2004 | Zaleski |
| 2005/0065471 A1 | 3/2005 | Kuntz |
| 2005/0124966 A1 | 6/2005 | Karpowicz et al. |
| 2005/0187528 A1 | 8/2005 | Berg |
| 2005/0209560 A1 | 9/2005 | Boukhny et al. |
| 2005/0256447 A1 | 11/2005 | Richardson et al. |
| 2005/0261805 A1 | 11/2005 | Mori et al. |
| 2006/0029675 A1 | 2/2006 | Ginther |
| 2006/0144440 A1 | 7/2006 | Merkle |
| 2006/0149171 A1 | 7/2006 | Vogel et al. |
| 2006/0229557 A1 | 10/2006 | Fathallah et al. |
| 2007/0005029 A1 | 1/2007 | Hopkins et al. |
| 2007/0016152 A1 | 1/2007 | Karpowicz et al. |
| 2007/0032741 A1 | 2/2007 | Hibner et al. |
| 2007/0032762 A1 | 2/2007 | Vogel |
| 2007/0032763 A1 | 2/2007 | Vogel |
| 2007/0078444 A1 | 4/2007 | Larsson |
| 2007/0118096 A1 | 5/2007 | Smith et al. |
| 2007/0179460 A1 | 8/2007 | Adahan |
| 2007/0180904 A1 | 8/2007 | Gao |
| 2007/0219480 A1 | 9/2007 | Kamen et al. |
| 2007/0233022 A1 | 10/2007 | Henley et al. |
| 2007/0260226 A1 | 11/2007 | Jaeb et al. |
| 2008/0005000 A1 | 1/2008 | Radl et al. |
| 2008/0015526 A1 | 1/2008 | Reiner et al. |
| 2008/0041401 A1 | 2/2008 | Casola et al. |
| 2008/0051708 A1 | 2/2008 | Kumar et al. |
| 2008/0071209 A1 | 3/2008 | Moubayed et al. |
| 2008/0071234 A1 | 3/2008 | Kelch et al. |
| 2008/0071235 A1 | 3/2008 | Locke et al. |
| 2008/0077091 A1 | 3/2008 | Mulligan |
| 2008/0082040 A1 | 4/2008 | Kubler et al. |
| 2008/0082077 A1 | 4/2008 | Williams |
| 2008/0091175 A1 | 4/2008 | Frikart et al. |
| 2008/0125697 A1 | 5/2008 | Gao |
| 2008/0125698 A1 | 5/2008 | Gerg et al. |
| 2008/0234641 A1* | 9/2008 | Locke ................ A61M 1/0031 604/313 |
| 2008/0243096 A1 | 10/2008 | Svedman |
| 2009/0005746 A1 | 1/2009 | Nielsen et al. |
| 2009/0037216 A1 | 2/2009 | Bluemler et al. |
| 2009/0043268 A1 | 2/2009 | Eddy et al. |
| 2009/0099867 A1 | 4/2009 | Newman |
| 2009/0101219 A1 | 4/2009 | Martini et al. |
| 2009/0206017 A1 | 8/2009 | Rohde et al. |
| 2009/0292264 A1 | 11/2009 | Hudspeth et al. |
| 2010/0022990 A1 | 1/2010 | Karpowicz et al. |
| 2010/0036333 A1 | 2/2010 | Schenk, III et al. |
| 2010/0042059 A1 | 2/2010 | Pratt et al. |
| 2010/0069829 A1 | 3/2010 | Hutchinson et al. |
| 2010/0114026 A1 | 5/2010 | Karratt et al. |
| 2010/0121257 A1 | 5/2010 | King |
| 2010/0126268 A1 | 5/2010 | Baily et al. |
| 2010/0145289 A1 | 6/2010 | Line et al. |
| 2010/0191178 A1 | 7/2010 | Ross et al. |
| 2010/0191199 A1 | 7/2010 | Evans et al. |
| 2010/0204663 A1 | 8/2010 | Wudyka |
| 2010/0211030 A1 | 8/2010 | Turner et al. |
| 2010/0268179 A1 | 10/2010 | Kelch et al. |
| 2010/0280435 A1 | 11/2010 | Raney et al. |
| 2010/0280536 A1 | 11/2010 | Hartwell |
| 2010/0305490 A1 | 12/2010 | Coulthard et al. |
| 2010/0305523 A1 | 12/2010 | Vess |
| 2010/0318043 A1 | 12/2010 | Malhi et al. |
| 2010/0318071 A1 | 12/2010 | Wudyka |

(56) References Cited

U.S. PATENT DOCUMENTS

| | | |
|---|---|---|
| 2011/0009824 A1 | 1/2011 | Yodfat et al. |
| 2011/0015587 A1 | 1/2011 | Tumey et al. |
| 2011/0028881 A1 | 2/2011 | Basaglia |
| 2011/0028882 A1 | 2/2011 | Basaglia |
| 2011/0034861 A1 | 2/2011 | Schaefer |
| 2011/0038741 A1 | 2/2011 | Lissner et al. |
| 2011/0040288 A1 | 2/2011 | Eckstein et al. |
| 2011/0054810 A1 | 3/2011 | Turner |
| 2011/0063117 A1 | 3/2011 | Turner |
| 2011/0066110 A1 | 3/2011 | Fathallah et al. |
| 2011/0071415 A1 | 3/2011 | Karwoski et al. |
| 2011/0077605 A1 | 3/2011 | Karpowicz et al. |
| 2011/0092927 A1 | 4/2011 | Wilkes et al. |
| 2011/0092958 A1 | 4/2011 | Jacobs |
| 2011/0106028 A1 | 5/2011 | Giezendanner et al. |
| 2011/0130712 A1 | 6/2011 | Topaz |
| 2011/0196321 A1 | 8/2011 | Wudyka |
| 2011/0251569 A1 | 10/2011 | Turner et al. |
| 2011/0257572 A1 | 10/2011 | Locke et al. |
| 2012/0001762 A1 | 1/2012 | Turner et al. |
| 2012/0035560 A1 | 2/2012 | Eddy et al. |
| 2012/0046625 A1 | 2/2012 | Johannison |
| 2012/0116334 A1* | 5/2012 | Albert ............ A61F 13/02 604/319 |
| 2012/0123323 A1 | 5/2012 | Kagan et al. |
| 2012/0123358 A1 | 5/2012 | Hall et al. |
| 2012/0157941 A1 | 6/2012 | Luckemeyer et al. |
| 2012/0181405 A1 | 7/2012 | Zlatic et al. |
| 2012/0184930 A1 | 7/2012 | Johannison |
| 2012/0184932 A1 | 7/2012 | Giezendanner et al. |
| 2012/0197196 A1 | 8/2012 | Halbert et al. |
| 2012/0203177 A1* | 8/2012 | Lanier, Jr. ......... A61M 5/14224 604/151 |
| 2012/0220960 A1 | 8/2012 | Ruland |
| 2012/0226247 A1 | 9/2012 | Danei et al. |
| 2012/0259283 A1 | 10/2012 | Haase |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |
| 2013/0023719 A1 | 1/2013 | Bennett |
| 2013/0062265 A1 | 3/2013 | Balschat et al. |
| 2013/0090613 A1 | 4/2013 | Kelch et al. |
| 2013/0123755 A1 | 5/2013 | Locke et al. |
| 2013/0144227 A1 | 6/2013 | Locke et al. |
| 2013/0165821 A1 | 6/2013 | Freedman et al. |
| 2013/0165877 A1 | 6/2013 | Leeson et al. |
| 2013/0267917 A1 | 10/2013 | Pan et al. |
| 2013/0267918 A1 | 10/2013 | Pan et al. |
| 2014/0058344 A1 | 2/2014 | Toth |
| 2014/0100516 A1 | 4/2014 | Hunt et al. |
| 2014/0114236 A1 | 4/2014 | Gordon |
| 2014/0114237 A1 | 4/2014 | Gordon |
| 2014/0163490 A1 | 6/2014 | Locke et al. |
| 2014/0194835 A1 | 7/2014 | Ehlert |
| 2014/0236106 A1 | 8/2014 | Locke et al. |
| 2014/0303551 A1 | 10/2014 | Germain et al. |
| 2014/0323906 A1 | 10/2014 | Peatfield et al. |
| 2015/0025482 A1 | 1/2015 | Begin et al. |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0174304 A1 | 6/2015 | Askem et al. |
| 2015/0261920 A1 | 9/2015 | Blick |
| 2015/0269323 A1 | 9/2015 | Ginsburg |
| 2017/0004106 A1 | 1/2017 | Joshua et al. |
| 2017/0007748 A1 | 1/2017 | Locke et al. |

FOREIGN PATENT DOCUMENTS

| | | |
|---|---|---|
| CN | 102049069 | 5/2011 |
| DE | 10 2010 036 405 | 1/2012 |
| EP | 1 684 146 | 7/2006 |
| EP | 2 066 365 | 4/2015 |
| GB | 2235877 | 3/1991 |
| WO | WO 1996/19335 | 6/1996 |
| WO | WO 2001/14048 | 3/2001 |
| WO | WO 2003/101508 | 12/2003 |
| WO | WO 2008/036344 | 3/2008 |
| WO | WO 2008/036360 | 3/2008 |
| WO | WO 2008/039223 | 4/2008 |
| WO | WO 2008/039314 | 4/2008 |
| WO | WO 2009/047524 | 4/2009 |
| WO | WO 2009/151645 | 12/2009 |
| WO | WO 2010/017484 | 2/2010 |
| WO | WO 2010/039481 | 4/2010 |
| WO | WO 2010/145780 | 12/2010 |
| WO | WO 2011/107972 | 9/2011 |
| WO | WO 2011/124388 | 10/2011 |
| WO | WO 2012/009869 | 1/2012 |
| WO | WO 2012/027342 | 3/2012 |
| WO | WO 2012/027913 | 3/2012 |
| WO | WO 2012/027914 | 3/2012 |
| WO | WO 2012/027915 | 3/2012 |
| WO | WO 2012/027916 | 3/2012 |
| WO | WO 2012/100624 | 8/2012 |
| WO | WO 2013/029330 | 3/2013 |
| WO | WO 2013/063848 | 5/2013 |
| WO | WO 2014/151930 | 9/2014 |
| WO | WO 2015/023515 | 2/2015 |
| WO | WO 2016/109048 | 7/2016 |

OTHER PUBLICATIONS

International Search Report and Written Opinion, re PCT Application No. PCT/US2014/026692, dated Mar. 2, 2015.
International Invitation to Pay and Partial Search Report, re PCT Application No. PCT/US2014/026692, dated Sep. 26, 2014.
International Search Report and Written Opinion, re PCT Application No. PCT/US2014/050233, dated Jan. 7, 2015.
International Search Report and Written Opinion, re PCT Application No. PCT/US2014/066441, dated Jun. 25, 2015.
International Search Report and Written Opinion, re PCT Application No. PCT/US2015/061430, dated Feb. 8, 2016.
"Vivano—Product application description," Hartmann Vivano, http://www.vivanosystem.info/20809.php, accessed Feb. 28, 2013.
International Preliminary Report on Patentability, re PCT Application No. PCT/US2015/061430, dated Jul. 13, 2017.

* cited by examiner

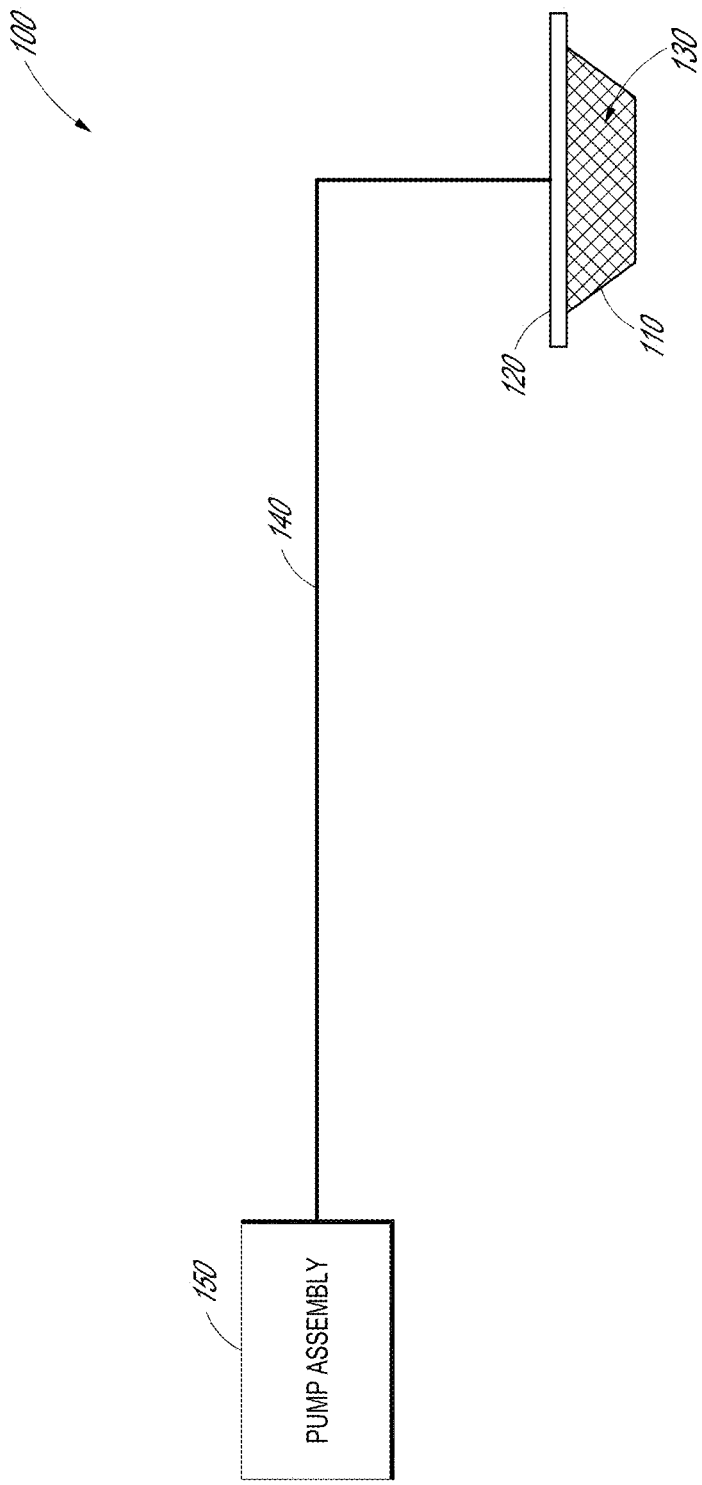

BLOCKAGE DETECTION IN REDUCED PRESSURE THERAPY

CROSS-REFERENCE TO RELATED APPLICATIONS

This application is a national stage application of International Patent Application No. PCT/US2015/061430, filed Nov. 18, 2015, which claims the benefit of U.S. Provisional Application Nos. 62/098,130 and 62/211,430 respectively filed Dec. 30, 2014, and Aug. 28, 2015; the disclosures of which are hereby incorporated by reference in their entireties.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

In some embodiments, an apparatus for applying negative pressure therapy is disclosed. The apparatus includes a housing and a controller. The housing includes a source of negative pressure. The source of negative pressure includes a pump configured to be in fluidic communication with a wound dressing via a fluid flow path. The controller is configured to operate the source of negative pressure. In addition, the controller is configured to (i) determine a level of activity of the pump, (ii) detect presence of a blockage in the fluid flow path using the level of activity of the pump and without using a pressure in the fluid flow path, and (iii) in response to detecting presence of the blockage in the fluid flow path, provide an indication of the blockage in the fluid flow path.

The apparatus of the preceding paragraph can include one or more of the following features: The controller is configured to determine the level of activity of the pump using a signal from a tachometer, and the signal is indicative of an operation of a motor of the pump. The controller is configured to (i) maintain a value in a memory responsive to the signal, the value being saturated when the level of activity of the pump is at or below a threshold level of activity and (ii) detect the presence of the blockage in response to determining that the value is saturated. The controller is configured to detect the presence of the blockage in response to determining that the value is saturated for a duration of time. The controller is configured to maintain the value in the memory by periodically adjusting the value responsive to the signal. The tachometer is external to the pump. The controller is configured to determine the level of activity of the pump from a duration of time between at least two consecutive pulses of the signal. The controller is configured to detect the presence of the blockage in response to determining that the duration of time between the at least two consecutive pulses satisfies a condition indicative of a blockage. The condition is a blockage threshold, and the controller is further configured to detect the presence of the blockage in response to determining that the duration of time between the at least two consecutive pulses exceeds the blockage threshold. The controller is configured to determine the level of activity of the pump from a duration of time between consecutive rising edges of the signal or consecutive falling edges of the signal. The controller is configured to (i) determine durations of time between at least two pulses of the signal and (ii) determine the level of activity of the pump from the determined durations of time. The controller is configured to (i) determine a variance of time between at least three pulses of the signal and (ii) determine the level of activity of the pump using the determined variance of time. The controller is configured to determine the level of activity of the pump from a change in a period of pulses of the signal. The controller is configured to (i) count a number of pulses of the signal for which a duration of time between consecutive pulses of the signal satisfies a condition and (n) determine the level of activity of the pump according to the count. The condition is a threshold, and the controller is configured to count the number of pulses of the signal for which the duration of time between consecutive pulses of the signal exceeds the threshold. The controller is configured to detect the presence of the blockage from a comparison of (i) a distribution pattern indicative of a blockage and (ii) a distribution of pulses of the signal over a period of time or a number of the pulses of the signal. The tachometer includes a Hall effect sensor. The controller is configured to detect the presence of the blockage in response to determining that the level of activity of the pump is indicative of an increased instability in operation of a motor of the pump. The controller is configured to detect the level of activity without using measurements output by the pump. The controller is configured to determine the level of activity of the pump using a signal from a tachometer internal to the pump, and the signal is an encoded motor signal indicative of motion of a motor of the pump. The controller is configured to determine the level of activity of the pump from a pulse width modulated signal used to drive a motor of the pump. The controller is configured to determine the level of activity of the pump from indications of use of a motor of the pump. The controller is configured to detect the presence of the blockage further using a change in the level of activity of the pump. The apparatus further includes a flow control valve disposed between the pump and either an inlet or outlet of the housing, and the flow control valve is configured to permit fluid flow through the flow control valve in only one direction. A flow control valve is not disposed between the pump and either an inlet or outlet of the housing. The indication of the blockage includes an alarm, and the controller is configured to activate the alarm in response to detecting presence of the blockage in the fluid flow path. The apparatus further includes a canister configured to collect fluid aspirated from under the wound dressing, and the blockage in the fluid flow path includes the canister being substantially full. The level of activity of the pump includes an operating speed of a pump motor. The apparatus further includes the wound dressing configured to be placed over a wound.

In sonic embodiments, a method of operating the apparatus of any of the preceding two paragraphs is disclosed.

BRIEF DESCRIPTION OF THE DRAWINGS

Embodiments of the present disclosure will now be described hereinafter, by way of example only, with reference to the accompanying drawings in which:

FIG. 1 illustrates a reduced pressure wound therapy system according to some embodiments.

DETAILED DESCRIPTION OF SOME EMBODIMENTS

Overview

Figure 2A:
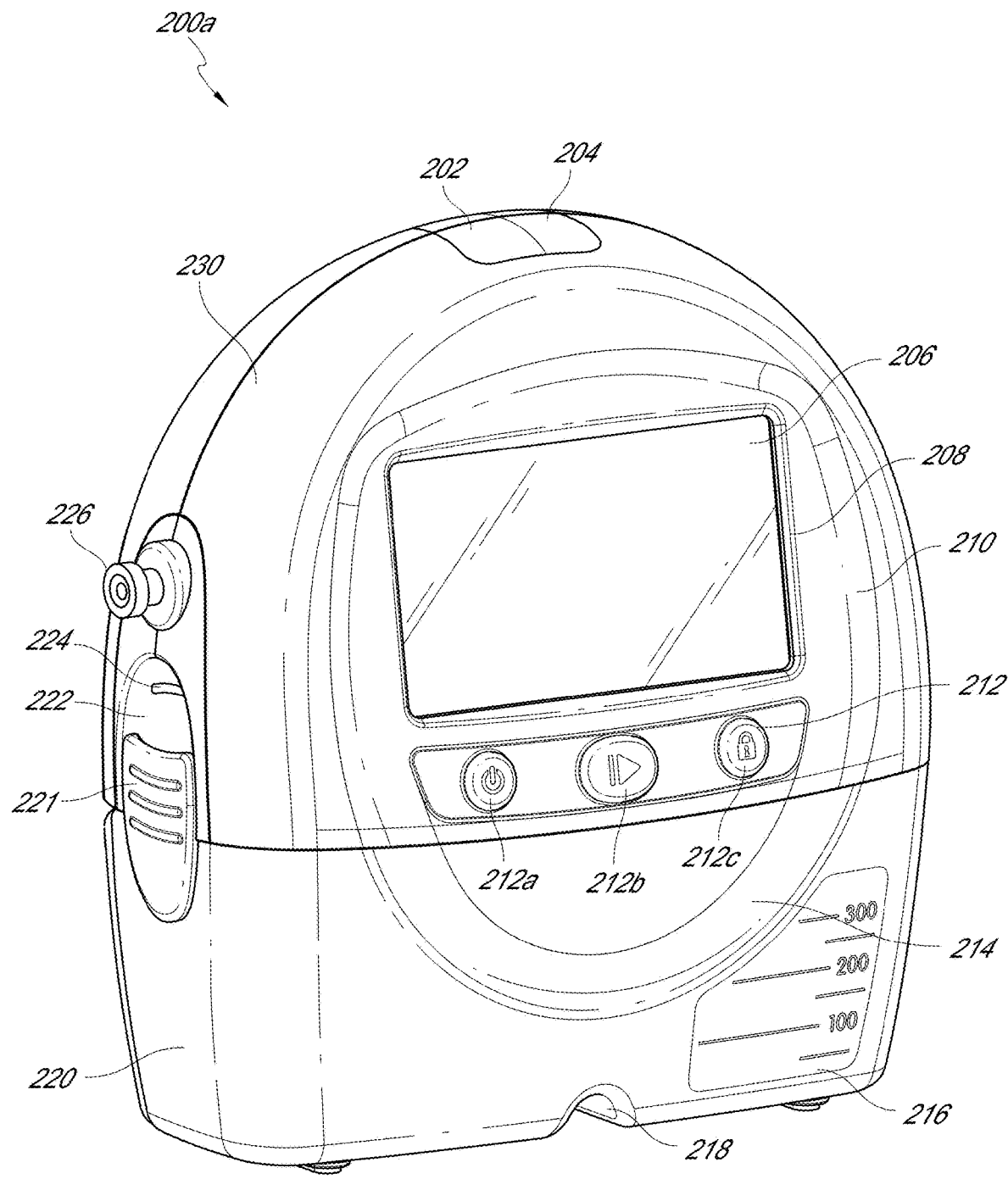
FIGS. 2A-2C illustrate a pump assembly and canister according to some embodiments.

Embodiments disclosed herein relate to systems and methods of treating a wound with reduced pressure. As is used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects relative pressure that is X mmHg below 760 mmHg or, in other words, an absolute pressure of (760–X) mmHg. In addition, negative pressure that is "less" or "smaller" than X mmHg corresponds to pressure that is closer to atmospheric pressure (e.g., –40 mmHg is less than –60 mmHg). Negative pressure that is "more" or "greater" than –X mmHg corresponds to pressure that is further from atmospheric pressure (e.g., –80 mmHg is more than –60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In sonic embodiments, configuring the pump assembly 150 and conduit 140 so that the conduit 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively, a pressure range of up to −75 mmHg, up to −80 mmHg or over −80 mmHg can be used. Also, a pressure range of below −75 mmHg can be used. Alternatively, a pressure range of over approximately −100 mmHg, or even 150 mmHg, can be supplied by the pump assembly 150.

In some embodiments, the pump assembly 150 is configured to provide continuous or intermittent negative pressure therapy. Continuous therapy can be delivered at above 25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first time duration, and upon expiration of the first time duration, negative pressure at high setpoint can be delivered for a second time duration. Upon expiration of the second time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Pump Assembly and Canister

FIG. 2A illustrates a front view 200A of a pump assembly 230, such as the pump assembly 150, and canister 220 according to some embodiments. As is illustrated, the pump assembly 230 and the canister 220 are connected, thereby forming a device. The pump assembly 230 comprises one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw a user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system, The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 comprises one or more keys or buttons 212 configured to allow the user to operate and monitor the operation of the TNP) system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
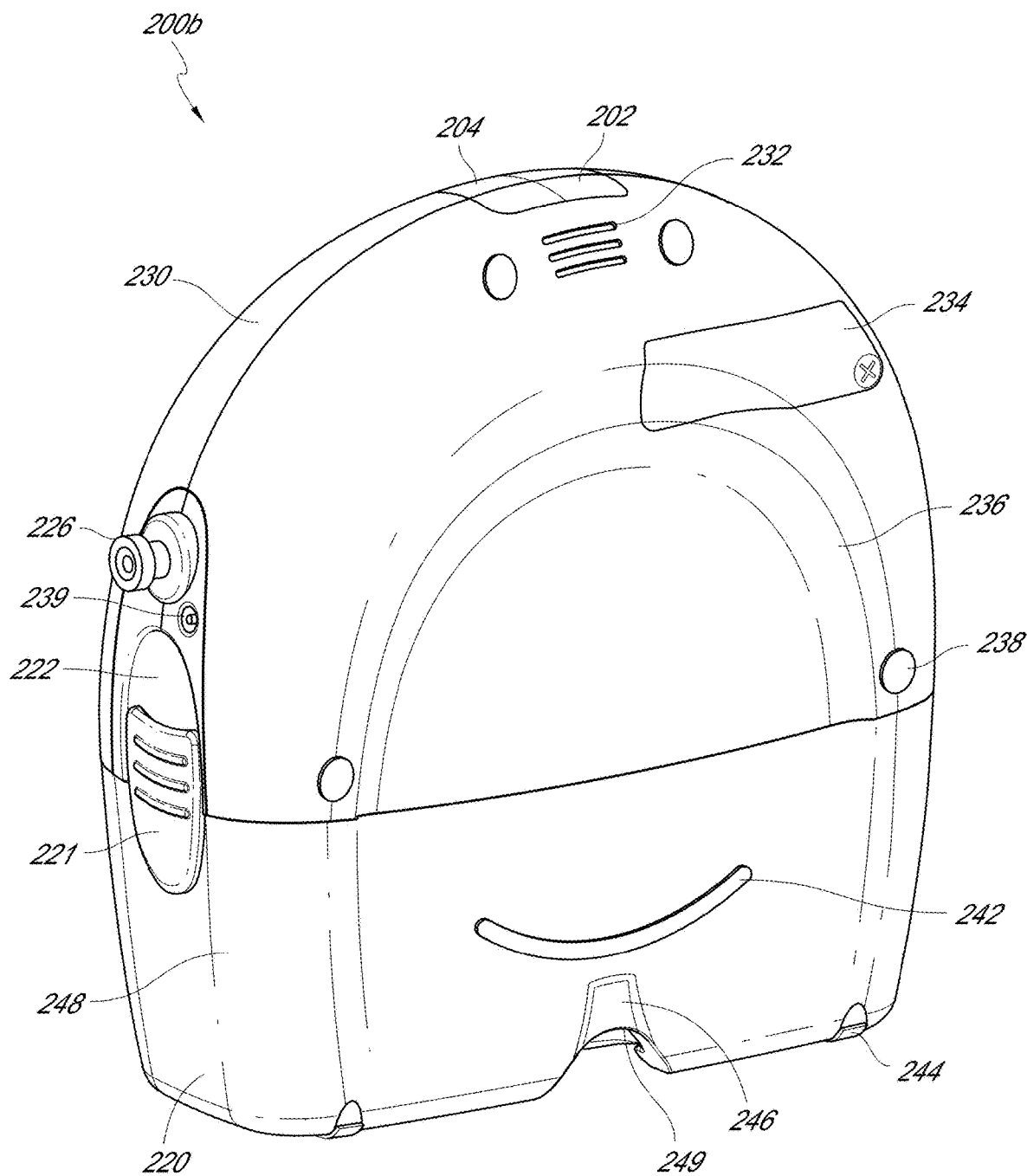

FIG. 2B illustrates a rear view 200B of the pump assembly 230 and canister 220 according to some embodiments. The pump assembly 230 comprises a speaker port 232 for producing sound. The pump assembly 230 includes a filter access door 234 for accessing and replacing one or more filters, such as antibacterial filters. The pump assembly 230 comprises a gripping portion 236 formed in the case of the pump assembly 230. The gripping portion 236 can be configured to allow the user to hold the pump assembly 230, such as during removal of the canister 220, The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly 230 can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can he configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
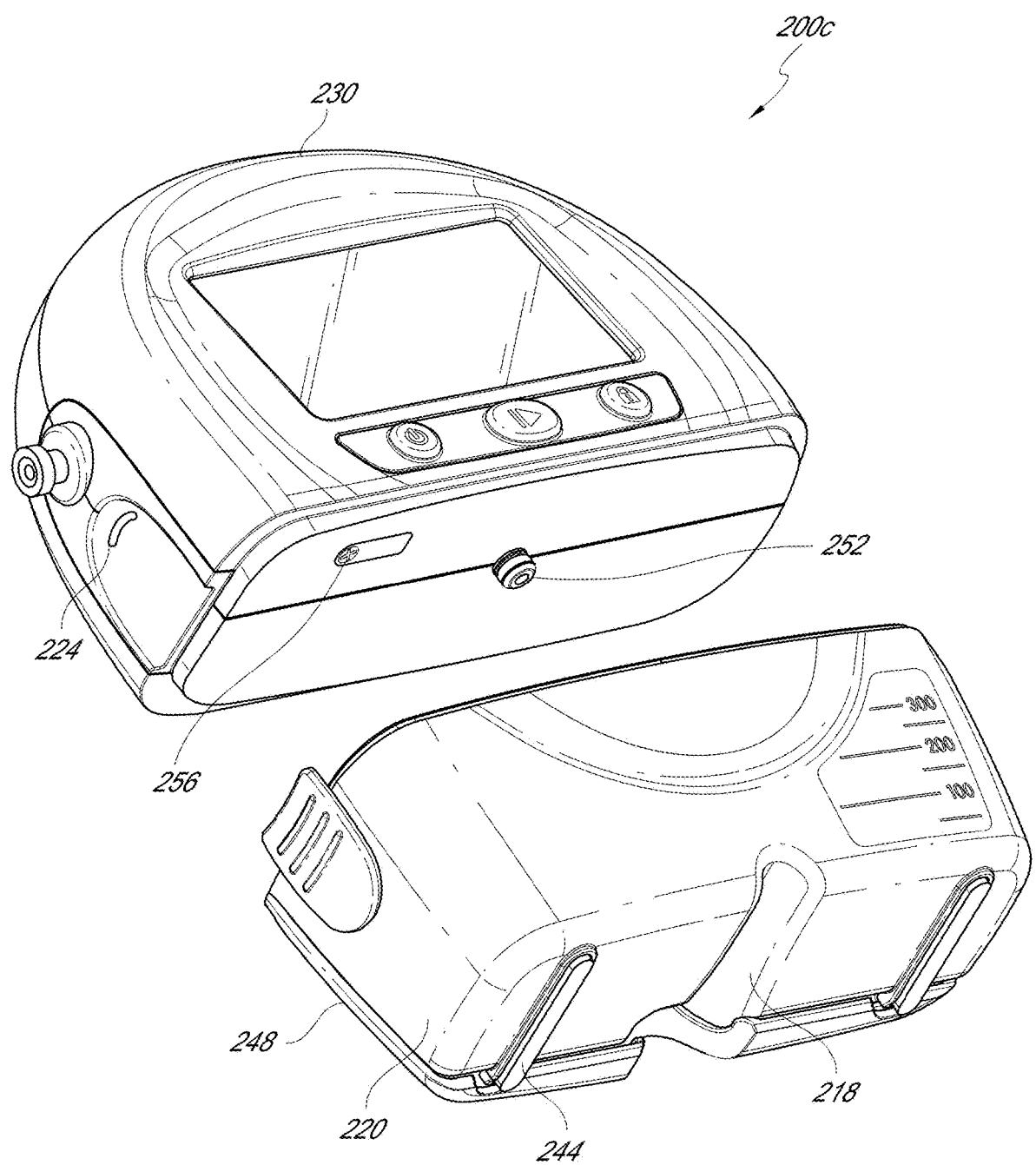

FIG. 2C illustrates a view 200C of the pump assembly 230 separated from the canister 220 according to some embodiments. The pump assembly 230 includes a vacuum attachment, connector, or inlet 252 through which a vacuum pump communicates negative pressure to the canister 220. The pump assembly 230 aspirates fluid, such as gas, from the wound via the inlet 252. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, or hybrid data transfer interfaces, such as SD, Compact Disc (CD), DVD, FireWire, Thunderbolt, PCI Express, and the like. In other embodiments, one or more of these additional ports are accessed through the door 234.

Additional description of the pump assembly 230 is disclosed in U.S. Patent Publication No. 2015/0025482, which is incorporated by reference in its entirety.

Pump Assembly Components

Figure 3A:
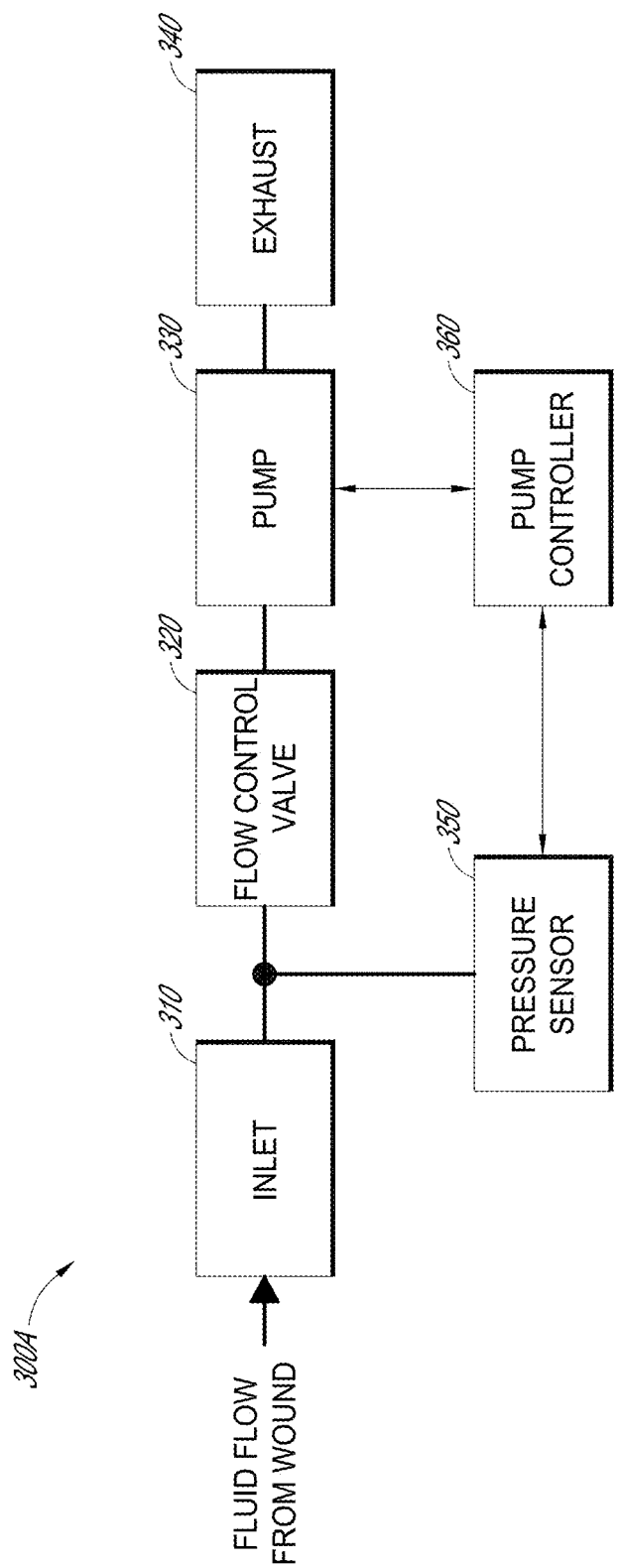
FIGS. 3A-3C illustrate block diagrams of components of a pump assembly according to some embodiments.

FIG. 3A illustrates a block diagram of certain components 300A of a pump assembly, such as the pump assembly 150, according to some embodiments. The components 300A include an inlet 310 (such as inlet 252), a flow control valve 320, a pump 330, an exhaust 340, a pressure sensor 350, and a pump controller 360.

The pump controller 360 can control the operation of the pump 330. The pump 330 can provide negative pressure in a fluid flow path connecting the inlet 310, the flow control valve 320, and the pump 330 such that the negative pressure is provided to the inlet 310 and then to a wound (for example, through a canister). The pump 330 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The flow control valve 320 can be a valve, such as a check valve like one commercially available from Value Plastics, Inc. or Qosina, Corp., that permits fluid flow through the valve in only one direction. In the illustration of FIG. 3A, the flow control valve 320 can allow fluid to flow in the fluid flow path from the inlet 310 to the exhaust 340, but not from the exhaust 340 to the inlet 310.

In some embodiments, the pump controller 360 can measure the pressure in the fluid flow path near or at the inlet 310 (or at any other location in the fluid flow path, such as at the wound), using data received from one or more pressure sensors, such as the pressure sensor 350, calculate the rate of fluid flow, and control the pump. In some embodiments, the pump controller 360 controls an actuator, such as a pump motor of the pump 330, so that a desired level of negative pressure is achieved in the wound cavity 110. The desired level of negative pressure (or negative pressure setpoint) can be a pressure set or selected by the user. In various embodiments, the pump controller 360 controls the pump 330 using pulse-width modulation (PWM), such as by controlling the pump motor of the pump 330 using PWM. A control signal for driving the pump 330 can be a 0-100% duty cycle PWM signal. The pump controller 360 can perform flow rate calculations and detect alarm conditions. The pump controller 360 can include internal memory (not shown) or utilize external memory (not shown), and the pump controller 360 can be a low-power processor.

In some embodiments, the pump controller 360 can, at least in sonic instances, control the pump 330, perform flow rate calculations, or detect alarm conditions without measuring or using measurements of the pressure in the fluid flow path or without using measurements output by the pump 330 (such as, a signal from an internal tachometer of the pump 330 that is responsive to a rotation of a pump motor of the pump). For example, the pump controller 360 can, at least in some instances, control the pump 330, perform flow rate calculations, or detect alarm conditions by using at least or only a level of activity of the pump 330 and without measuring or using measured pressure in the fluid flow path. As another example, the pump controller 360 can control the pump 330, perform flow rate calculations, or detect alarm conditions using at least or only measurements of the pressure in the fluid flow path and without determining or using the determined level of activity of the pump. This can be performed, for instance, by comparing the magnitude of a detected pressure signal to one or more thresholds, such as a blockage threshold to determine an occlusion or blockage in the fluid flow path. One or more pulses detected or sensed by the pressure sensor can be determined as exceeding (or meeting or falling below) the blockage threshold. When the number of such pulses meets a threshold (such as exceeds, becomes equal to, or falls below), determination of a blockage can be made. Another condition can be that time between pulses that meet the blockage threshold. When such time meets a threshold (such as exceeds, becomes equal to, or falls below), determination of a blockage can be made. Using a level of activity of a pump to determine or estimate flow may be in contrast with direct measurement of flow rate, such as by using a flow meter. In various embodiments, determination of canister full, leakage, and the like can additionally or alternatively be made.

The components 300A can further include one or more additional sensors (not shown), such as a tachometer, positioned to detect or determine a level of activity of the pump 330 and provide indications responsive to the level of activity of the pump 330 to the pump controller 360. For example, a tachometer can be separate from the pump 330 (for example, external to the pump) and positioned near or coupled to the pump 330, and the tachometer can detect a rotation (such as a partial rotation, complete rotation, or multiple partial or complete rotations) of a pump motor of the pump 330. The tachometer can output a signal (or signals) that provide the indications, such as pulses (for example, high signal indications in a series of otherwise low signal indications), responsive to the rotation of the pump motor to the pump controller 360. The tachometer can be a Hall effect sensor or opto-isolator sensor in some implementations.

The pump controller 360 can perform flow rate monitoring for the fluid flow path using the indications from the one or more additional sensors, The pump controller 360 can continuously or periodically monitor the indications from the one or more additional sensors to monitor the flow rate. For example, the pump controller 360 can receive the signal including indications from a tachometer and thereby determine a rotation speed (sometimes referred to as an operating speed) of the pump motor of the pump 330. If the rotation speed may be below, at, or above a certain level, for instance, it can be determined that a blockage (sometimes referred to as a limited volume condition) may be present in the fluid flow path. The blockage can be due to a blockage in a tube or lumen, canister being full, etc. An alarm can be triggered by the pump controller 360 in such instances, and the pump controller 360 can wait for a user to take one or more actions to resolve the blockage. In some embodiments, at least in sonic instances, the pump controller 360 can control the pump, perform flow rate calculations, or detect alarm conditions using the indications responsive to the level of activity of the pump 330 and without using measurements of the pressure in the fluid flow path or without using measurements output by the pump 330.

Figure 3B:
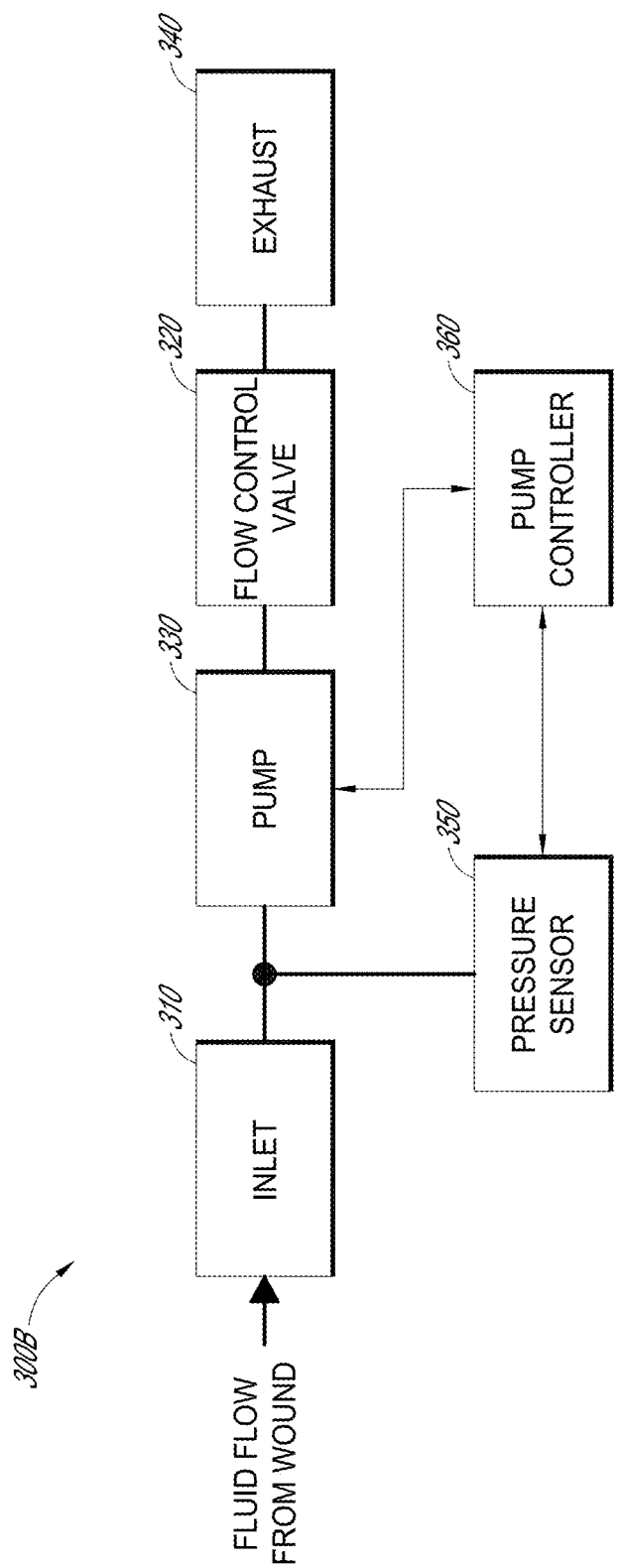

FIG. 3B illustrates a block diagram of certain components 300B of a pump assembly, such as the pump assembly 150, according to some embodiments. The components 300B can be the same as the components 300A of FIG. 3A except that the position of the pump 330 and flow control valve 320 in the fluid flow path can be switched. Thus, the flow control valve 320 can be positioned on the exhaust-side of the pump 330 in the fluid flow path as illustrated in FIG. 3B, rather than the inlet-side of the pump 330 in the fluid flow path as illustrated in FIG. 3A.

Figure 3C:
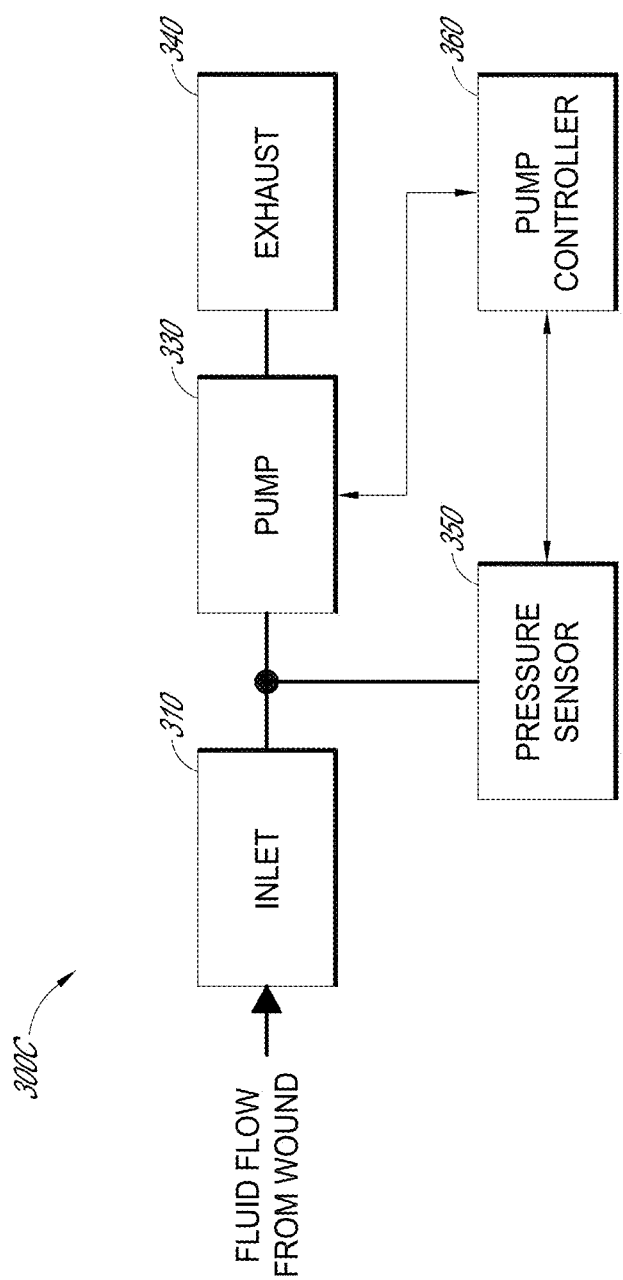

FIG. 3C illustrates a block diagram of components 300C of a pump assembly, such as the pump assembly 150, according to some embodiments. The components 300C can be the same as the components 300A of FIG. 3A except that the flow control valve 320 may not be included in the fluid flow path as illustrated in FIG. 3C. In certain embodiments, a flow control valve can be integrated into the pump 330.

Blockage Detection

Figure 4:
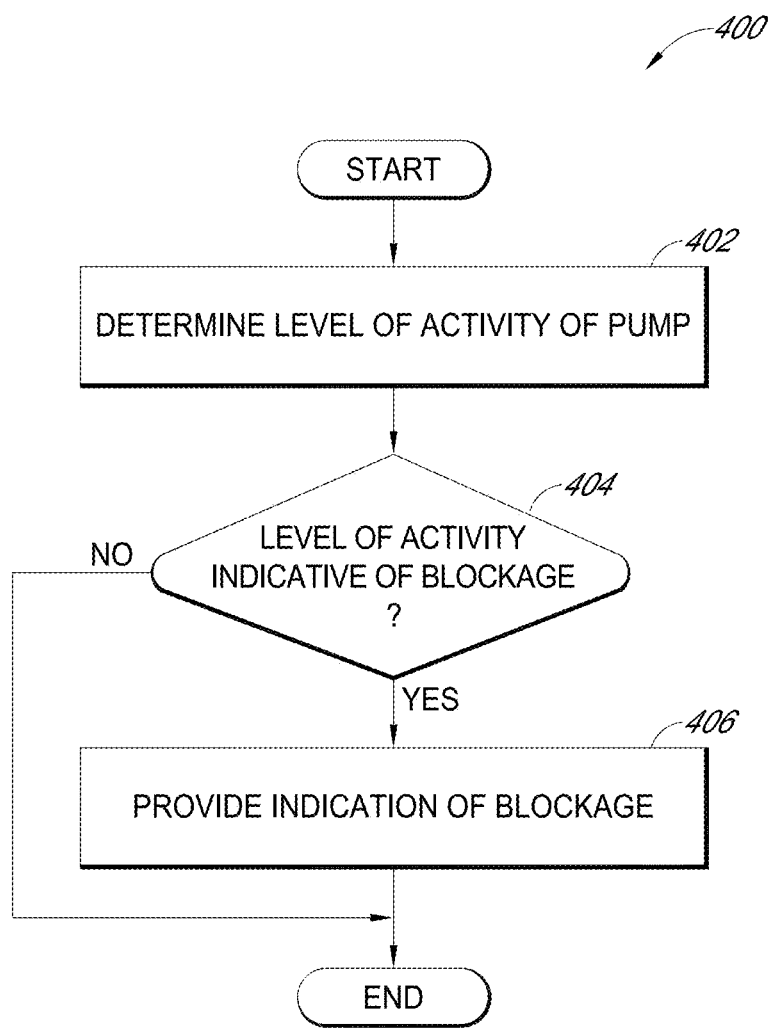
FIG. 4 illustrates a process of providing an indication of a blockage according to some embodiments.

FIG. 4 illustrates a process 400 of providing an indication of a blockage in a fluid flow path according to some embodiments. The process 400 can be executed by the pump controller 360, for example. The process 400 can be continuously or periodically executed or at any other suitable frequency. Advantageously, in certain embodiments, the process 400 can enable an indication of a blockage in a fluid flow path to be provided without using the pressure in the fluid flow path or without using measurements output by the pump to detect the blockage.

At block 402, the process 400 can determine a level of activity of a pump, such as the pump 330. The level of activity of the pump can be determined continuously or periodically or at any other suitable frequency. In one example, the level of activity of the pump can be determined according to a level of activity of a pump motor of the pump that is detected by a sensor, such as a tachometer. The tachometer can detect a rotation of the pump motor and provide a signal including indications, such as pulses, responsive to the rotation. In another example, the level of activity of the pump can be determined using a PWM signal used to drive the pump motor, an encoded signal output by the pump, or the pressure in the fluid flow path. In certain embodiments, one or more of these or other determinations can be combined to calculate the level of activity.

In some embodiments, the level of activity of the pump can be determined using a signal (for example, a signal output by a tachometer) by determining if one or more conditions have been met or satisfied. In some embodiments, one or more of the following can be determined: (1) a duration of time between consecutive features of the signal, (2) multiple durations of time between multiple features of the signal, (3) a variance of time between features of the signal (for example, average period), (4) a count of a number of features of the signal for which a duration of time between consecutive features of the signal exceeds (or meets or falls below) a threshold value, and (5) a range of time between features of the signal. The features (sometimes referred to as pulses) of the signal can be, for instance, one or more of a rising edge of the signal, a falling edge of the signal, a peak of the signal, and a trough of the signal. In another example, the level of activity of the pump can be determined according to a PWM signal used to drive the pump motor or an encoded motor signal output by the pump. The process 400 can, in some embodiments, further determine a change in the level of activity of the pump over time at block 402. The change in the level of activity of the pump can be determined continuously or periodically or at any other suitable frequency. In some embodiments, the level of activity or change in the level of activity can be further processed, such as averaged, filtered, and the like.

At block 404, the process 400 can determine whether the level of activity of the pump is indicative of a blockage in a fluid flow path. The fluid flow path can provide for fluidic communication between a wound dressing, such as the wound cover 120, and the pump, and the blockage can be a condition indicative of a substantially full canister or dressing or that a canister or dressing filter may be occluded or blocked. In one example, the level of activity of the pump can be indicative of the blockage when the level or the change in level of activity of the pump satisfies (for instance, meets, falls below, or exceeds) one or more thresholds or matches one or more patterns (such as (i) a certain number of the last total number of pulses of a signal exceed a limit, (ii) repeated long delays in pulses of a signal followed by a short delay in one or more pulses of the signal, or (iii) a value tracked by a processor, like the pump controller 360, and responsive to pulses of a signal remains constant or substantially constant (for instance, the signal become saturated because a frequency in the pulses of the signal is so low that data collection capabilities of the sensor(s) or processor prevent the processor from further adjusting the value)). In another example, the level of activity of the pump can be indicative of the blockage when the level of activity shows an increased instability in the operation of the pump. The increased instability can, for instance, be evidenced in pump control behavior when the pump repeatedly overshoots a pump control setpoint, decays from a pump control setpoint, or accelerates from a pump control setpoint. As another example, as explained herein, increased instability can be manifested via unstable levels of pump activity, such as when a variance of measured pump activity meets (such as exceeds or falls below) a threshold.

Figure 5A:
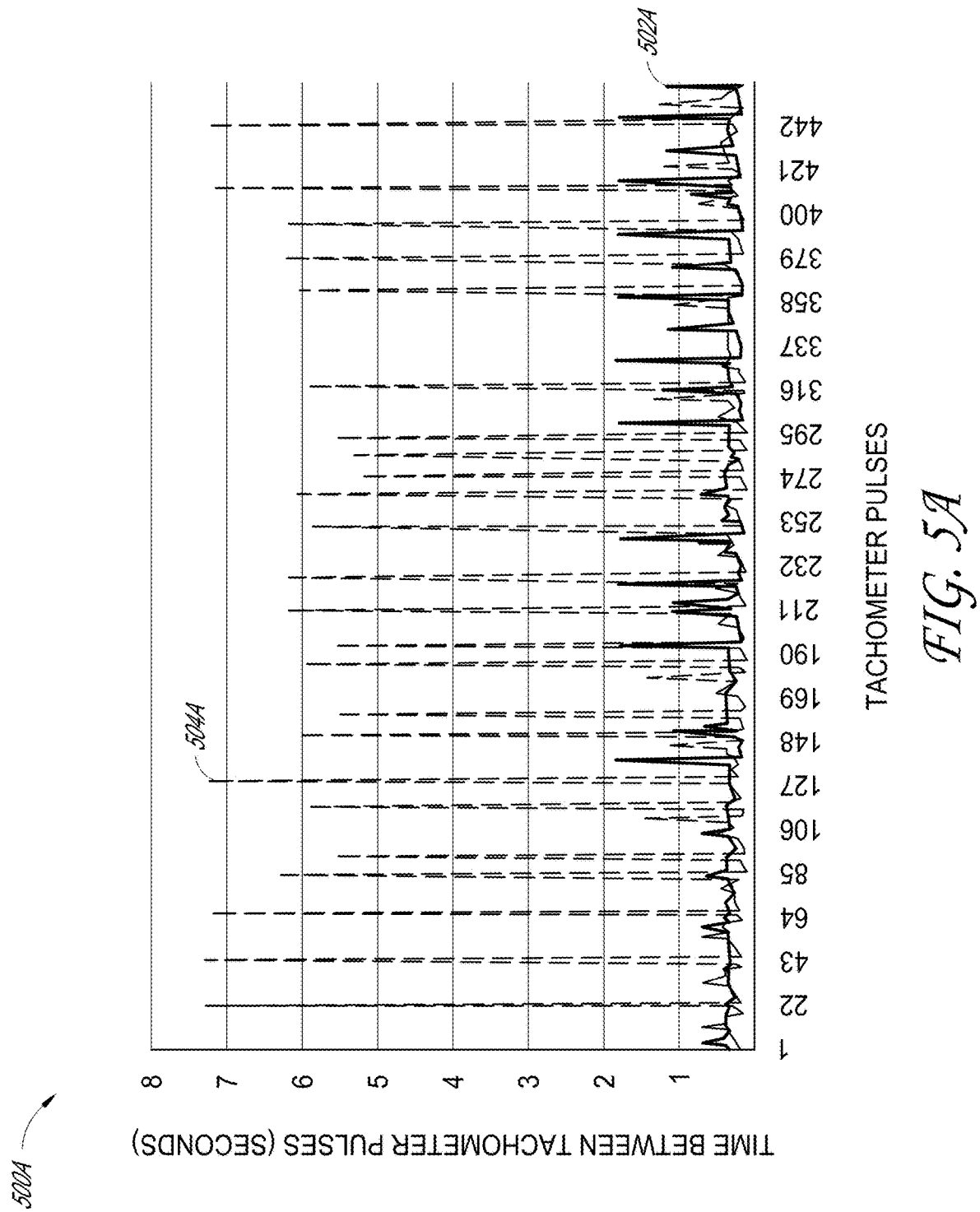
FIGS. 5A-5C show plots illustrating when a level of activity of a pump may be indicative a blockage according to some embodiments.
Figure 5B:
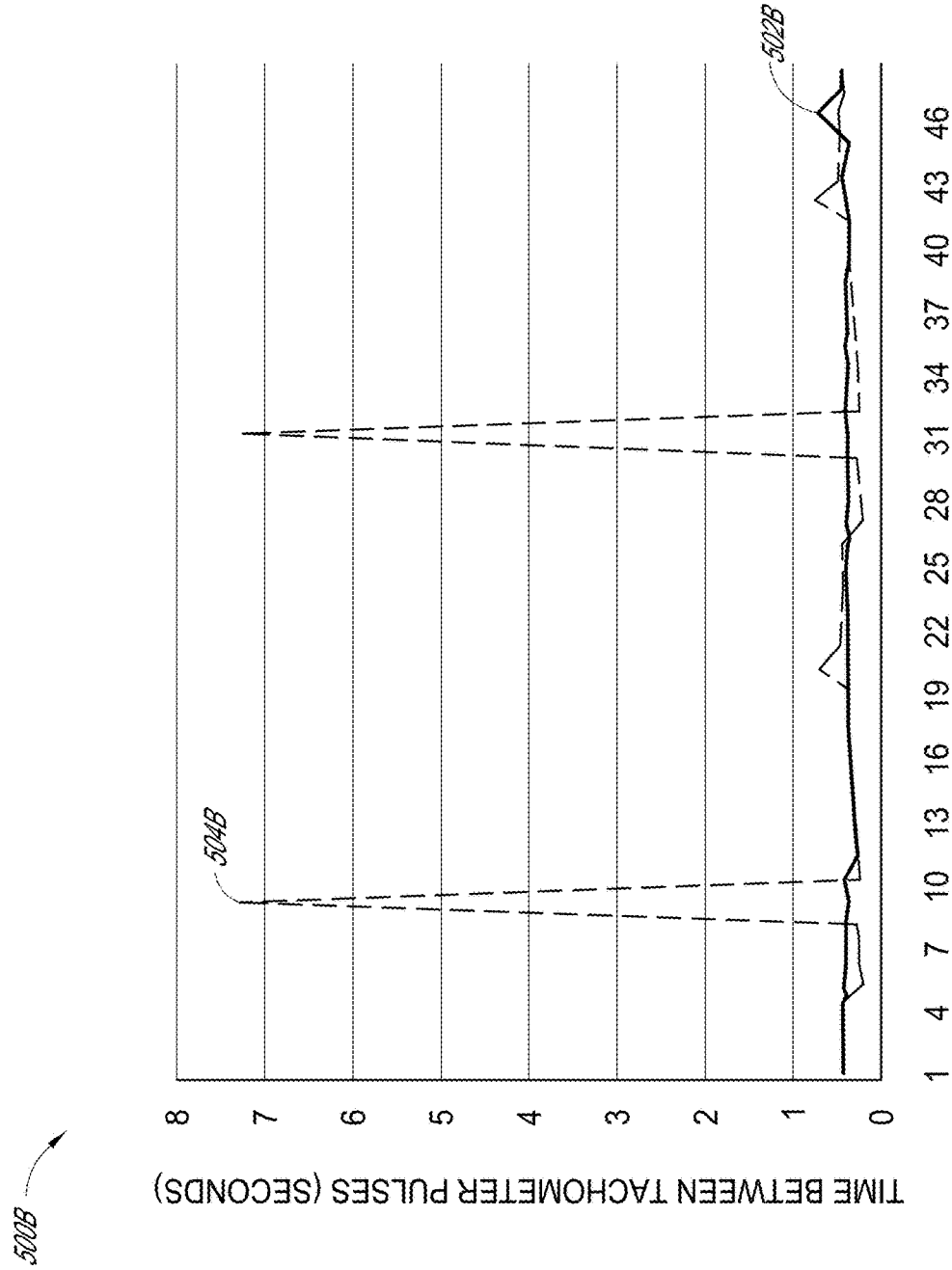
Figure 5C:
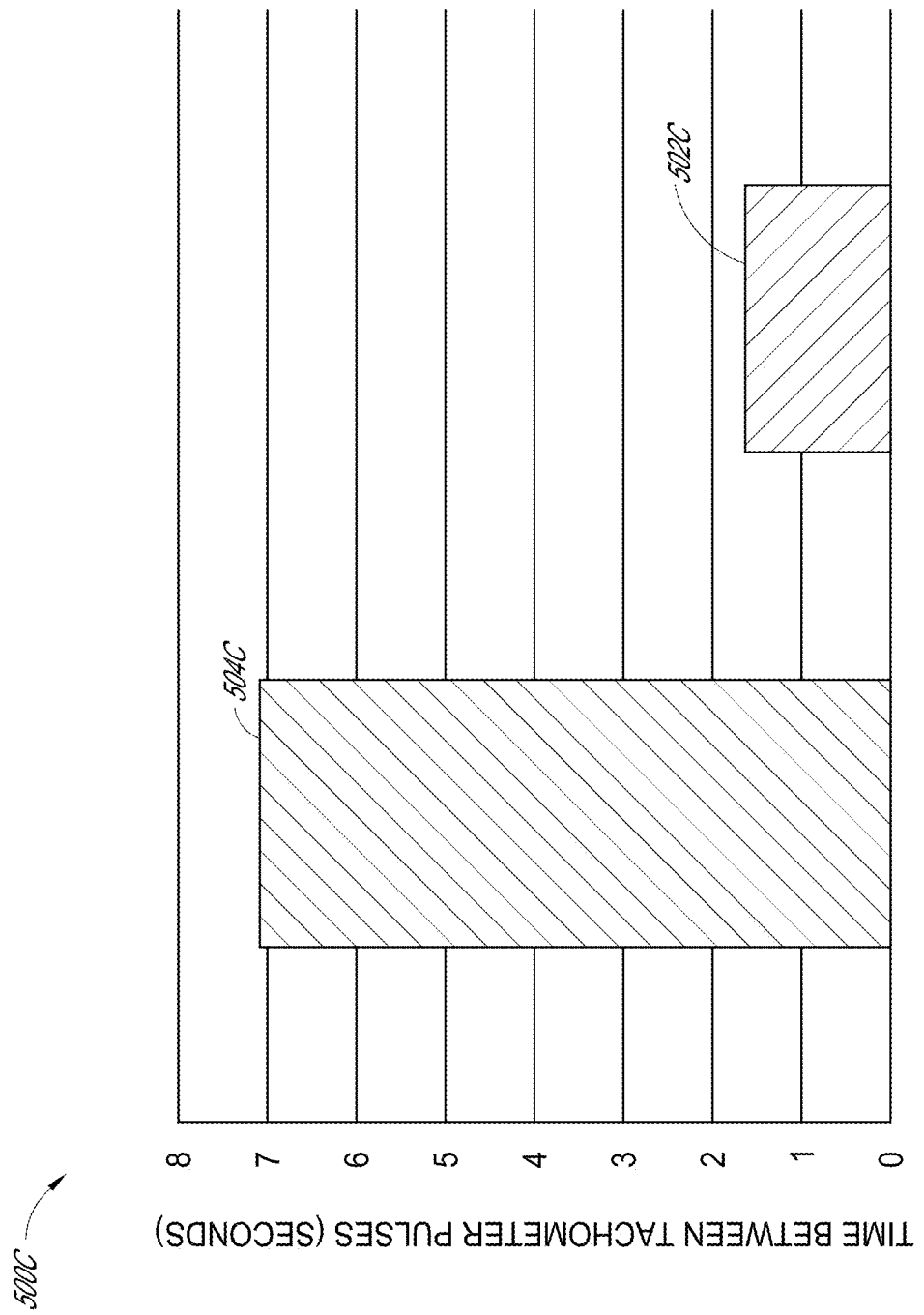

Example levels of activity or changes in a level of activity of a pump over time that may be indicative or not indicative of the blockage are described at least with respect to FIGS. 5A-5C. Other example levels of activity or changes in the level of activity of the pump over time that may be indicative or not indicative of the blockage will be apparent from reviewing at least the described example levels or changes described herein.

If the level of activity of the pump over time is not indicative of the blockage in the fluid flow path, the process 400 can end, or in some embodiments, one or more other checks can be performed using different approaches to determine whether a blockage is present. On the other hand, if the level of activity of the pump over time is indicative of the blockage in the fluid flow path, the process 400 can move to block 406. At block 406, the process 400 can provide an indication of the blockage. The indication of the blockage can, for example, include activating an alarm denoting the blockage. The alarm can, in turn, direct a user to investigate or resolve the blockage. In some instances, the indication of the blockage can denote a potential blockage condition rather than definitively indicating a blockage condition. In some embodiments, the process 400 can also perform one or more other checks using different approaches to confirm the presence of a blockage. In another example, the indication of the blockage can include changing an operating mode of the pump, such as deactivating the pump, triggering a countdown timer for deactivating the pump if the blockage is not resolved within a period of time, or increasing or decreasing the level of activity of the pump.

In certain embodiments, executing the process 400 can provide one or more different advantages. In one example, the process 400 can be desirable for use with a pump controller or pump that may be relatively cheap, simple, or have limited capabilities. This can be because the process 400 may use relatively straightforward techniques (for example, determining a duration of time between features of a signal, a counting features of a signal and then comparing the duration or count to a threshold, or detecting saturation for a period of time in a tracked value responsive to pulses of a signal) to determine whether to provide an indication of a blockage, and thus may be incorporated into a pump controller or pump that is relatively inexpensive and simple. In another example, using the process 400 can be desirable because a pump assembly, such as the pump assembly 150, may not include a pressure sensor, such as the pressure sensor 350, to determine whether to provide an indication of a blockage or may not include a pump that outputs a signal indicative of the level of activity of the pump. As a result, the cost of the pump assembly can be reduced, and the size of the pump assembly may also be decreased. In yet another example, using the process 400 can be desirable for increasing the robustness or accuracy of determining whether to provide an indication of a blockage. The process 400 can, for instance, be used in combination with or independently from one or more other blockage determinations (for example, blockage determinations based on pressure measurements, weight measurements, or optical detection in a canister or a fluid flow path) to make a final determination of whether to provide an indication of a blockage. The process 400 can additionally be advantageous because the process 400 may detect a blockage when one or more other blockage determinations may fail to detect the blockage. For instance, when other processing (for example, averaging) may be performed on measurements from a sensor detecting the level of activity of a pump (for instance, an operating speed), such processing may smooth or mask a blockage from being noted from the processed signal, while the blockage may be readily detectable using the approaches provided herein. In one illustration, six tachometer pulses every 60 seconds may produce the same calculated average as five tachometer pulses respectively separated by 180 seconds, 20 seconds, 40 seconds, 60 seconds, and 60 seconds. However, the five tachometer pulses may be indicative of a blockage as described herein while the six tachometer pulses may not be indicative of a blockage. In some embodiments, the process 400 can distinguish between various types of blockage conditions, such as between canister (or dressing) full and blockage in other portions of the flow path.

FIG. 5A shows an example plot 500A illustrating when a level of activity of a pump, such as the pump 330, may be indicative a blockage according to some embodiments. The plot 500A can be a plot for a pump assembly, such as the pump assembly 230, which includes the components 300A, 300B, or 300C discussed with respect to FIGS. 3A-3C, as well as a tachometer configured to provide pulses indicative of a rotation of a pump motor of the pump. The y-axis of the plot 500A provides a time between consecutive tachometer pulses in seconds, and the x-axis of the plot 500A provides an assigned numbering for approximately 450 consecutive tachometer pulses. Curve 502A illustrates data obtained for a flow path that does not have a blockage, and curve 504A illustrates data obtained from a flow path with a blockage.

The plot 500A illustrates, for instance, how a longer duration between tachometer pulses or consecutive tachometer pulses can be indicative of a blockage, such as a full canister (or dressing). Based on the plot 500A, as one example, a threshold can be set such that when a time between consecutive tachometer pulses exceeds about 2 seconds, the level of activity of the pump can be considered indicative of a blockage. As another example, the threshold can be set to about 3 seconds, 4 seconds, etc.

FIG. 5B shows an example plot 500B illustrating when a level of activity of a pump, such as the pump 330, may be indicative a blockage according to some embodiments. The plot 500B can be a plot for a pump assembly, such as the pump assembly 230, which includes the components 300A, 300B, or 300C discussed with respect to FIGS. 3A-3C, as well as a tachometer configured to provide pulses indicative of a rotation of a pump motor of the pump. The y-axis of the plot 500B provides a time between consecutive tachometer pulses in seconds, and the x-axis of the plot 500B provides an assigned numbering for approximately 50 consecutive tachometer pulses (as opposed to about 450 pulses in FIG. 5A). Curve 502B illustrates data obtained for a flow path that does not have a blockage, and curve 504B illustrates data obtained from a flow path with a blockage.

The plot 500B illustrates, for instance, how a longer duration between consecutive tachometer pulses can be indicative of a blockage, such as a full canister (or dressing) condition. Based on the plot 500B, as one example, a threshold can be set such that when a time between consecutive tachometer pulses exceeds about 1 second, the level of activity of the pump can be considered indicative of a blockage. As another example, the threshold can be set to about 2 seconds, 3 seconds, etc.

FIG. 5C shows an example plot 500C illustrating when a level of activity of a pump may be indicative a blockage according to some embodiments. The plot 500C can be a plot for a pump assembly, such as the pump assembly 230, Which includes the components 300A, 300B, or 300C discussed with respect to FIGS. 3A-3C, as well as a tachometer configured to provide pulses indicative of a rotation of a pump motor of the pump. The y-axis of the plot 500C provides a minimum observed time between tachometer pulses in seconds, and the x-axis of the plot 500C shows a restricting canister condition or empty canister condition. Curve 502C illustrates data obtained for a flow path that does not have a blockage, and curve 504C illustrates data obtained from a flow path with a blockage.

The plot 500C illustrates, for instance, how a longer duration between minimum observed times between tachometer pulses or consecutive tachometer pulses can be indicative of a blockage, such as a canister (or dressing) full canister. Based on the plot 500C, as one example, a threshold can be set such that when a minimum observed time between consecutive tachometer pulses exceeds 2 seconds, the level of activity of the pump can be considered indicative of a blockage. As another example, the threshold can be set to about 3 seconds, 4 seconds, etc.

Figure 6:
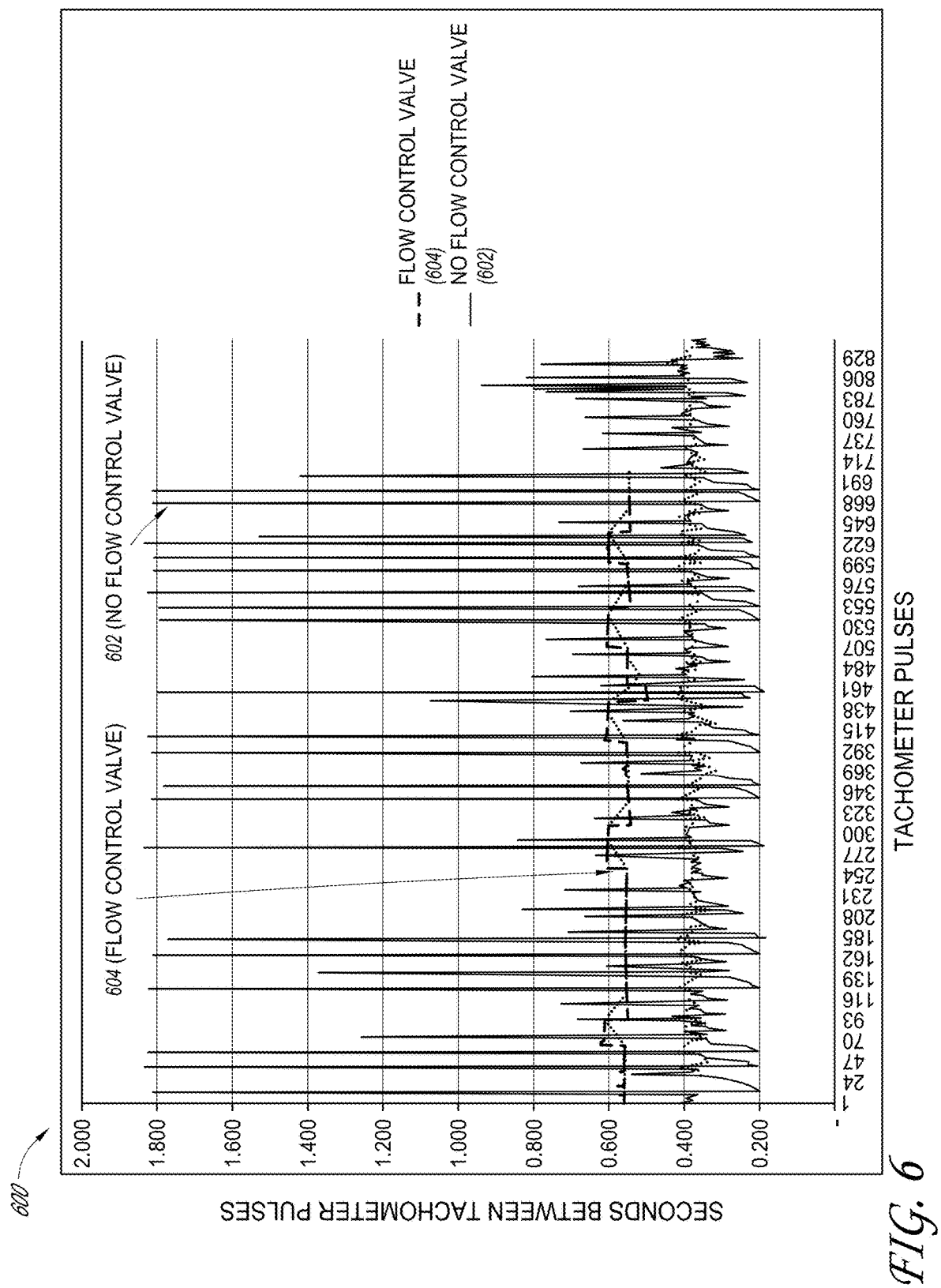
FIG. 6 shows a plot illustrating the impact of a flow control value in a fluid flow path according to some embodiments.

FIG. 6 shows an example plot 600 illustrating the impact of a flow control value in a fluid flow path on a detected signal usable to determine a level of activity of a pump according to some embodiments. The plot 600 can be a plot for a pump assembly, such as the pump assembly 230, which includes the components 300A or 300B in the case of the flow control valve line and the components 300C in the case of the no flow control valve line, as well as a tachometer configured to provide pulses indicative of a rotation of a pump motor of the pump. The y-axis of the plot 600 provides a time between consecutive tachometer pulses in seconds, and the x-axis of the plot 600 provides an assigned numbering for approximately 850 consecutive tachometer pulses. Curve 602 illustrates data obtained for a pump assembly without a flow control valve, and curve 604 illustrates data obtained for a pump assembly with a flow control valve. The plot 600 further depicts moving averages for the curves 602, 604 that can be processed in addition to or in place of the curves 602, 604 in some embodiments.

The plot 600, for instance, illustrates how, in certain embodiments, the inclusion of the flow control valve in the fluid flow path can result in more stable pump activity and, in turn, more stable or accurate measurements from a sensor, such as a tachometer, positioned to detect or determine the level of activity of the pump. Moreover, in addition to the flow direction control benefits of the flow control valve, the flow control valve can reduce pressure waves in the fluid flow path by providing a pressure drop and functioning as a low-pass filter for pressure signals traveling to the pump. The inclusion of the flow control valve can further help with preventing nuisance to user caused by spurious activation of pump assembly alarms. In various embodiments, duration between non-consecutive pulses can be utilized. In some embodiments, measure of variance of the level of activity of the pump, such as an average tachometer period, can be used in addition to or instead of duration between features of the level of activity, such as duration between consecutive tachometer pulses. This is described in connection with FIGS. 8A-8B and 9A-9B, for example.

Figure 7:
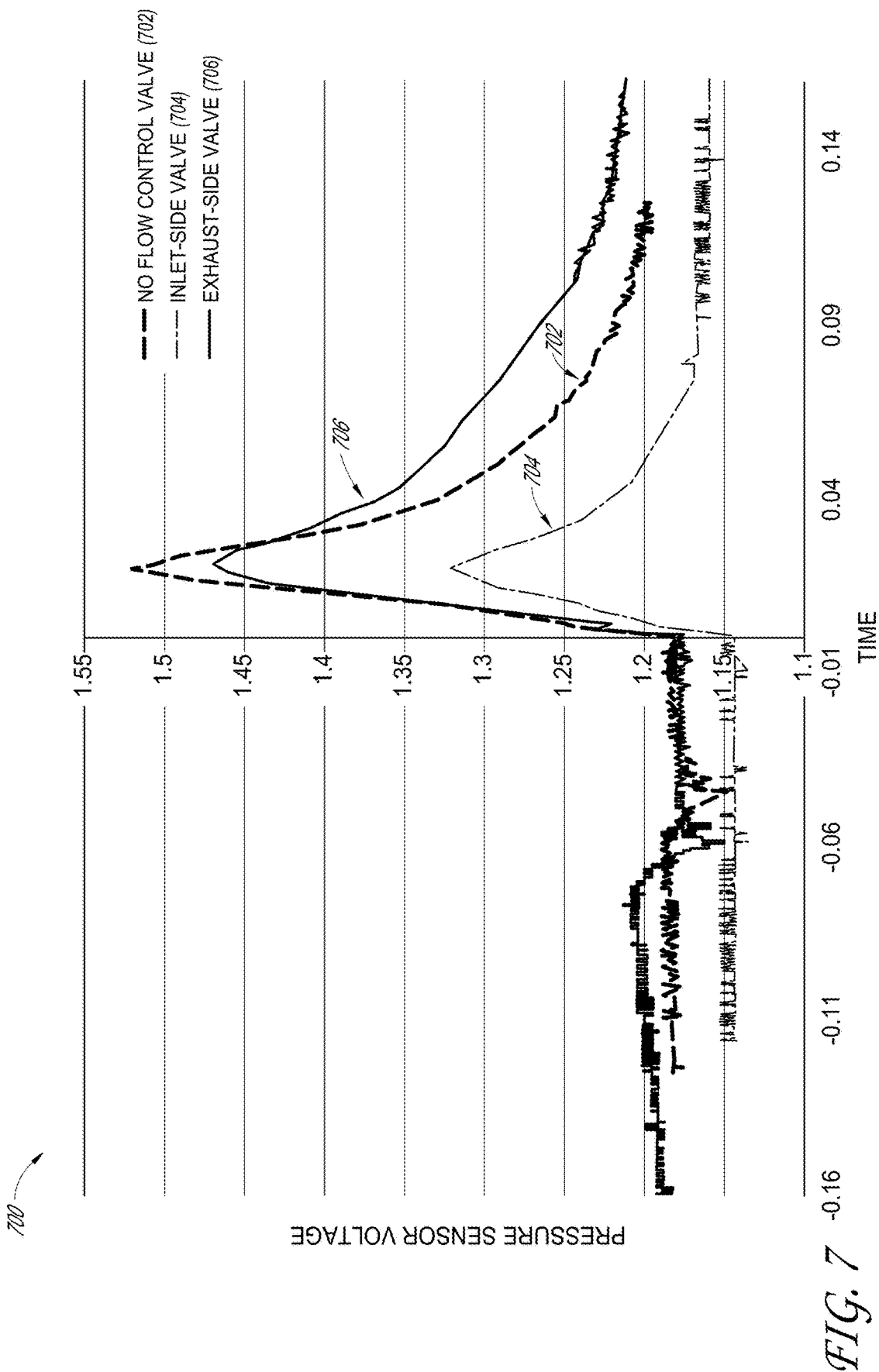
FIG. 7 shows a plot illustrating the impact of a flow control value in various positions in a fluid flow path according to some embodiments.

FIG. 7 shows an example plot 700 illustrating the impact of a flow control value in various positions in a fluid flow path on a detected signal usable to determine a level of activity of a pump according to some embodiments. The plot 700 can be a plot for a pump assembly, such as the pump assembly 230, which includes the arrangement of the components 300A in the case of the inlet-side valve line 704, the arrangement of the components 300B in the case of the exhaust-side valve line 706, and the components 300C in the case of the no flow control valve line 702, as well as a tachometer configured to provide pulses indicative of a rotation of a pump motor of the pump. The y-axis of the plot 700 provides a pressure sensor voltage for a pressure sensor, such as the pressure sensor 350, and the x-axis of the plot 700 provides time.

The plot 700, for instance, illustrates how, in certain embodiments, the inclusion of the flow control valve in the fluid flow path can result in attenuated or reduced pressure waves (for example, by providing a pressure drop and functioning as a low-pass filter for pressure signals traveling to the sensor). As is illustrated by curve 704, which corresponds to the arrangement of the components 300A of FIG. 3A, inclusion of a flow control valve at the inlet can advantageously reduce pressure waves and result in more accurate, stable, greater signal amplitude measurements from one or more sensors, such as a an activity sensor (for example, a tachometer), than other arrangements or combinations of components. As is explained in connection with FIGS. 8A-8B and 9A-8B, this can provide for improved discrimination during processing of the sensed signal. The inclusion of the flow control valve can further help with preventing nuisance to user caused by spurious activation of pump assembly alarms.

Blockage Detection Using Clamped State Detection

Figure 8A:
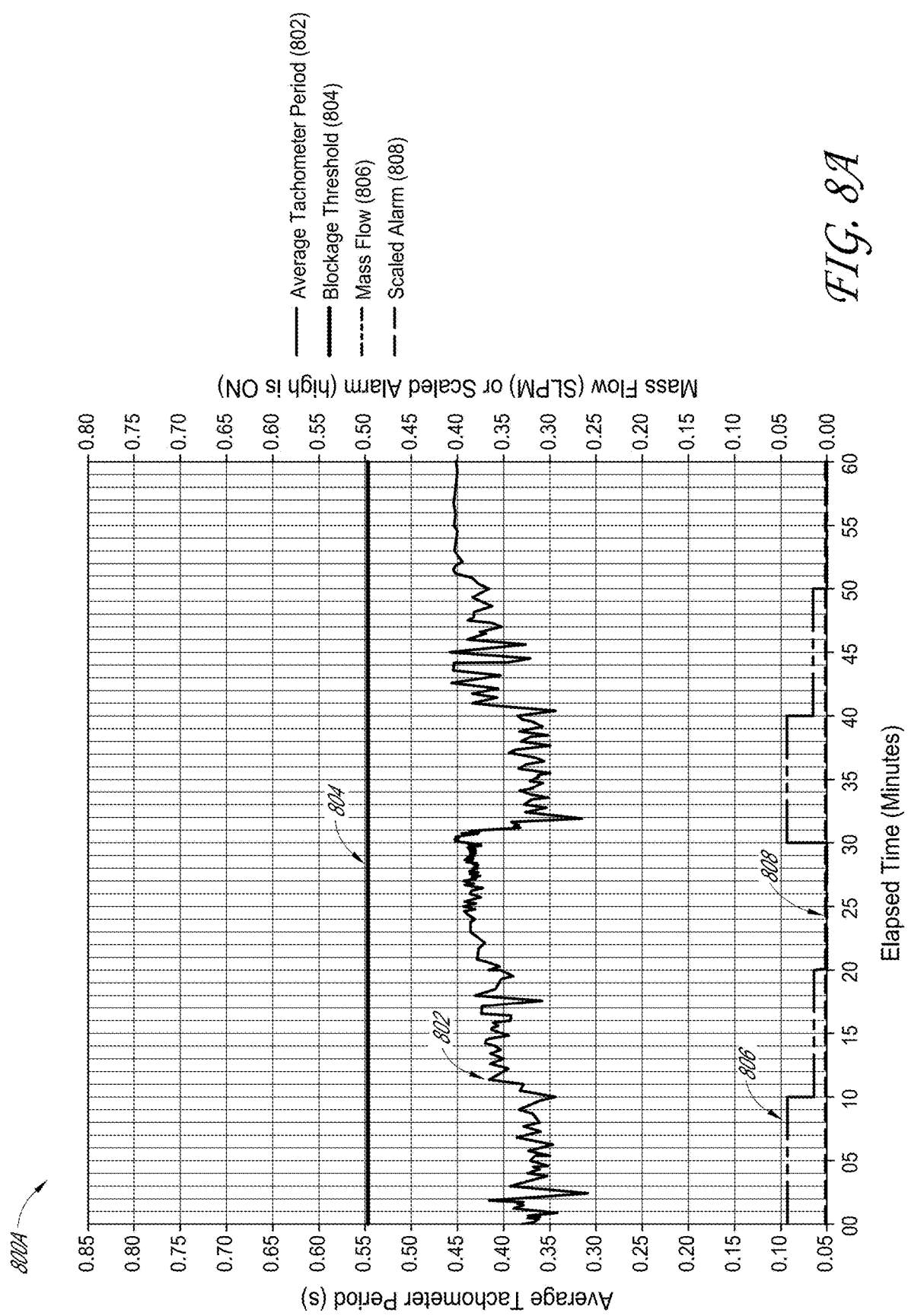
FIGS. 8A-8B and 9A-9B show example plots illustrating when a level of activity of a pump may be indicative a blockage according to some embodiments.

FIG. 8A shows an example plot 800A illustrating when a level of activity of a pump, such as the pump 330, may be indicative of a blockage according to some embodiments. The plot 800A can be a plot for a pump assembly, such as the pump assembly 230, which includes the components 300C discussed with respect to FIG. 3C, as well as a tachometer configured to provide pulses indicative of a rotation of a pump motor of the pump. The pump assembly can be operating at a setpoint of −40 mmHg. The y-axis of the plot 800A provides an average time period (or frequency) between consecutive tachometer pulses in seconds (scale on the left), mass flow measure in standard liter per minute (SLPM) (scale on the right), and scaled alarm indication (high corresponds to "ON"). The x-axis of the plot 800A provides elapsed time in minutes. The plot 800A depicts an average tachometer period 802, a blockage threshold setting 804, a mass flow measurement 806 (for example, flow rate directly measured using a flow meter, such as a mass flow meter), and a scaled alarm 808 over time. The scaled alarm 808 can be indicative of an alarm condition, such as a blockage condition, when high. The scaled alarm 808 can, for instance, (i) be used to activate and deactivate an alarm, which can be audibly or visually perceptible, (ii) be an alarm flag in memory, or (iii) involve or trigger changing operation of the pump.

The plot 800A illustrates, for instance, how the scaled alarm 808 may not be activated when the average tachometer period 802 does not satisfy the blockage threshold 804. As can be seen, the average tachometer period 802 remains below the blockage threshold 804 such that the scaled alarm 808 remains deactivated. However, the mass flow measurement 806 illustrates little to no flow in the fluid flow path, which is indicative of a blockage condition.

Figure 8B:
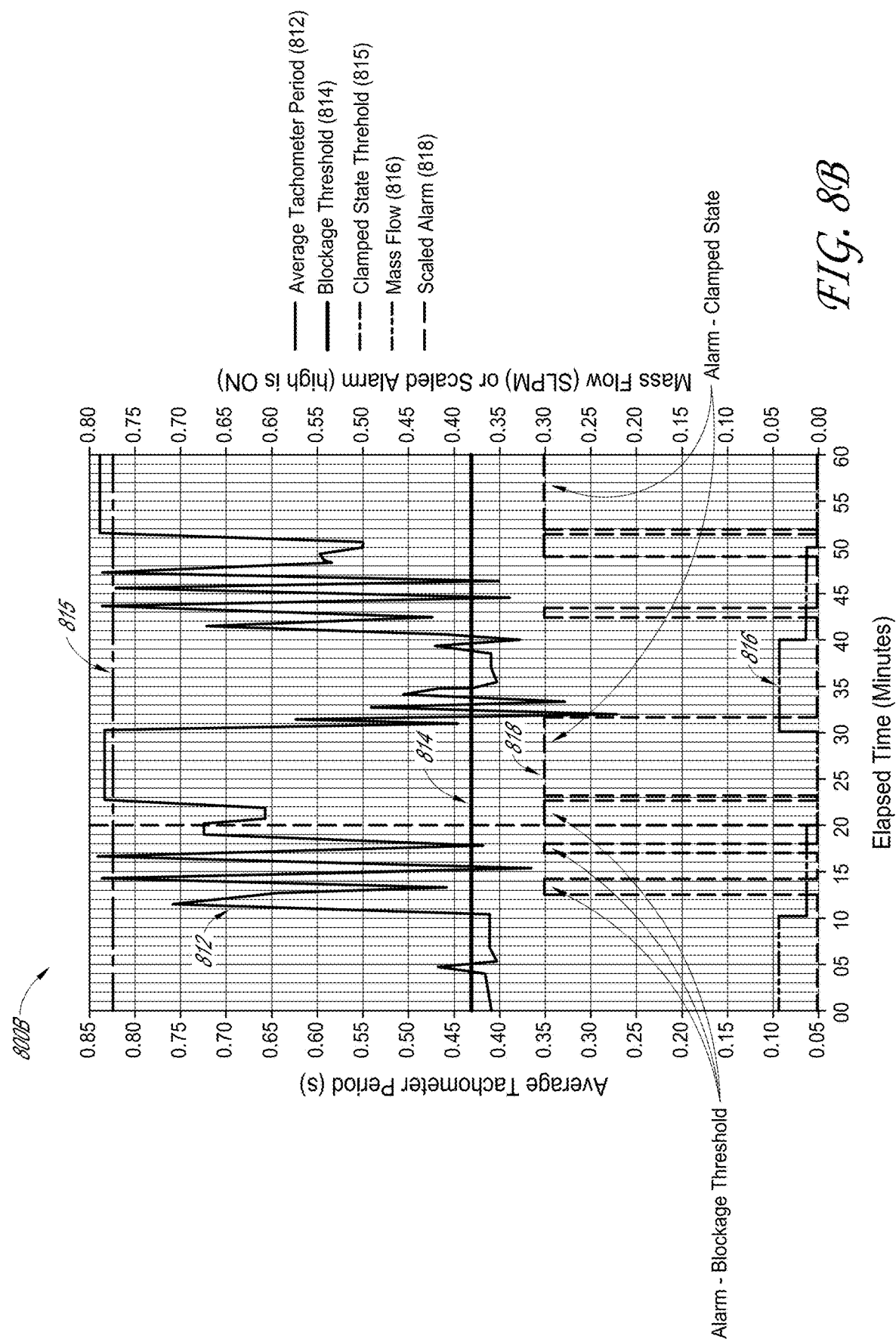

FIG. 8B shows an example plot 800B illustrating when a level of activity of a pump, such as the pump 330, may be indicative a blockage according to some embodiments. The plot 800B can be a plot for a pump assembly, such as the pump assembly 230, which includes the components 300A discussed with respect to FIG. 3A, as well as a tachometer configured to provide pulses indicative of a rotation of a pump motor of the pump. The pump assembly can be operating at a setpoint of −40 mmHg. The y-axis of the plot 800B provides an average time period between consecutive tachometer pulses in seconds (scale on the left), mass flow measure in SLPM (scale on the right), and scaled alarm indication (high corresponds to "ON"). The x-axis of the plot 800B provides elapsed time in minutes. The plot 800B depicts an average tachometer period 812, a blockage threshold setting 814, a clamped state threshold 815, a mass flow measurement 816, and a scaled alarm 818 over time. The scaled alarm 818 can be indicative of an alarm condition, such as a blockage condition, when high. The scaled alarm 818 can, for instance, (i) be used to activate and deactivate an alarm, which can be audibly or visually perceptible, (ii) be an alarm flag in memory, or (iii) involve or trigger changing operation of the pump. In comparison with the average tachometer period 802 of FIG. 8A (which is obtained from a pump that does not include a fluid control valve), the average tachometer period 812 has larger, more accurate amplitude or dynamic range, so that accuracies of processing and detection are improved. In some embodiments, period of time between consecutive tachometer pulses (such as for example in FIGS. 5A-5C and 6) or any other measure of the level of activity can be utilized instead of or in addition to the average tachometer period.

The plot 800B illustrates, for instance, how the scaled alarm 818 may be activated when the average tachometer period 812 satisfies at least one of the blockage threshold setting 814 or the clamped state threshold setting 815 instantaneously or for a period of time (for example, 10 seconds, 20 seconds, 30 seconds, 45 seconds, 1 minute, 1.5 minutes, 2 minutes, 3 minutes, etc.). As can be seen, the scaled alarm 818 may not be activated at around 4 minutes because the average tachometer period 812 may not have satisfied the blockage threshold setting 814 or the clamped state threshold setting 815. On the other hand, the scaled alarm 818 can be activated at around 12 minutes and 17 minutes when the average tachometer period 812 satisfies the blockage threshold setting 814. Activation of the scaled alarm 818 at around 12 minutes and 17 minutes can thus be used to trigger a blockage threshold alarm. The scaled alarm 818 activated at around 12 minutes and 17 minutes can be deactivated at around 14 minutes and 18 minutes when the average tachometer period 812 may no longer satisfy the blockage threshold setting 814. In addition, the scaled alarm 818 may be activated at around 23 minutes when the average tachometer period 812 satisfies the clamped state threshold setting 815. Activation of the scaled alarm 818 at around 23 minutes can thus be used to trigger a clamped state threshold alarm. The scaled alarm 818 activated at around 23 minutes can be deactivated at around 32 minutes when the average tachometer period 812 may no longer satisfy one or both of the blockage threshold setting 814 or the clamped state threshold setting 815. This operation can be confirmed by the mass flow measurement 816, which illustrates little to no flow in the fluid flow path, which is indicative of a blockage condition. Moreover, the mass flow measurement 816 at around between 0-10 minutes and around between 30-40 minutes can represent a minimum allowable flow for a pump assembly. As a result, an alarm during around between 0-10 minutes and around between 30-40 minutes can be considered a nuisance alarm. In addition, the mass flow measurement 816 at around between 10-30 minutes and around between 40-60 minutes can be less than the minimum allowable flow for the pump assembly, so an alarm may be expected and triggered as described herein. After an alarm is triggered, the mass flow measurement 816 can return to the minimum allowable state, and the alarm can be then cleared as illustrated at around 31 minutes.

Clamped state detection can be performed using the clamped state threshold setting 815, which can be a threshold for the pump that depends on the data collection capabilities of the pump. The pump can track a value, such as the average tachometer period 812 (or count of tachometer pulses and the like), responsive to the level of activity of the pump. In some instances, however, because the pump may be operating slowly due to a blockage in a flow path (for instance, pump motor may be turning slowly), sensed indication of the pump activity may become unreliable. For example, the time between tachometer pulses may become so long due to the blockage so that it meets a threshold (for instance, exceed or fall below the threshold) that corresponds to a cut off for collecting meaningful data. This condition may be referred to as recording a saturated value or reaching a "clamped state." Clamped state may be reached for various reasons, including, for example, due to one or more sensors or a pump controller (for instance, the pump controller 360) of the pump being relatively cheap, simple, or having limited capabilities (for instance, processing speed, memory, etc.). In clamped state, the determined value corresponding to the level of activity may saturate and remain constant for a period of time because the value may be unable to be further increased or decreased (in other words, the value becomes saturated) even though the value should further change responsive to the level of activity of the pump according to the function which is used to adjust the value. Advantageously, in certain embodiments, the saturation of such a value can provide an indication of an irregular condition for the pump and a more reliable and faster indication of a blockage than some other approaches.

In one example, a pump controller of a pump may have a capacity to track a level of activity of the pump using a value stored using 8 bits of data (this is, the level of activity can be tracked with a granularity of 256 levels ranging from the level 0 to the level 255) where the level 255 can be indicative of a lowest assigned level of activity and the level 0 can be indicative of a highest assigned level of activity. In this example, the level of activity of the pump may drop below the lowest assigned level of activity and thus the pump controller may consider the level of activity to remain at the 255 level even though the level of activity has decreased below lowest assigned level of activity. Therefore, when the value remains at the 255 level and thus saturates, the saturation of the value can indicate an irregular operating condition for the pump and can be used as an alarm condition indicative of a blockage. In some embodiments, to prevent intermittent alarms, which may be a nuisance to the user, the saturation of the value may be considered an alarm condition once the value remains saturated for a period of time, such as 30 seconds, 1 minute, 2 minutes, and the like.

in some embodiments, checking for the clamped state using a clamped state threshold results in more accurate and reliable blockage detection than only using a blockage threshold. This is because meeting the clamped threshold can reliably indicate that a pump is operating very slowly due to a permanent blockage in a fluid flow path. In contrast, relying on the blockage threshold alone may result in less stable and accurate detection at least because a pump controller may not differentiate between (i) a temporary blockage (which may become cleared and should not trigger a blockage alarm) and (ii) a permanent blockage in the fluid flow path. On the other hand, meeting the clamped state threshold, which is selected to signal a very low activity of the pump as compared to the blockage threshold, can indicate that a severe blockage is present and that such blockage is unlikely to be a temporary blockage. Accordingly, blockage condition may be triggered more accurately and reliably when the clamped state threshold is used. Although the plot 800B illustrates simultaneous use of the blockage threshold 814 and the clamped state threshold 815, the blockage threshold 814 and the clamped state threshold 815 can each be implemented independently or without one threshold or the other. In addition, in some embodiments, the scaled alarms 808 and 818 can be used, alone or in combination, with one or more other conditions or indications (for example, such as those disclosed herein) to determine whether to activate an alarm.

Figure 9A:
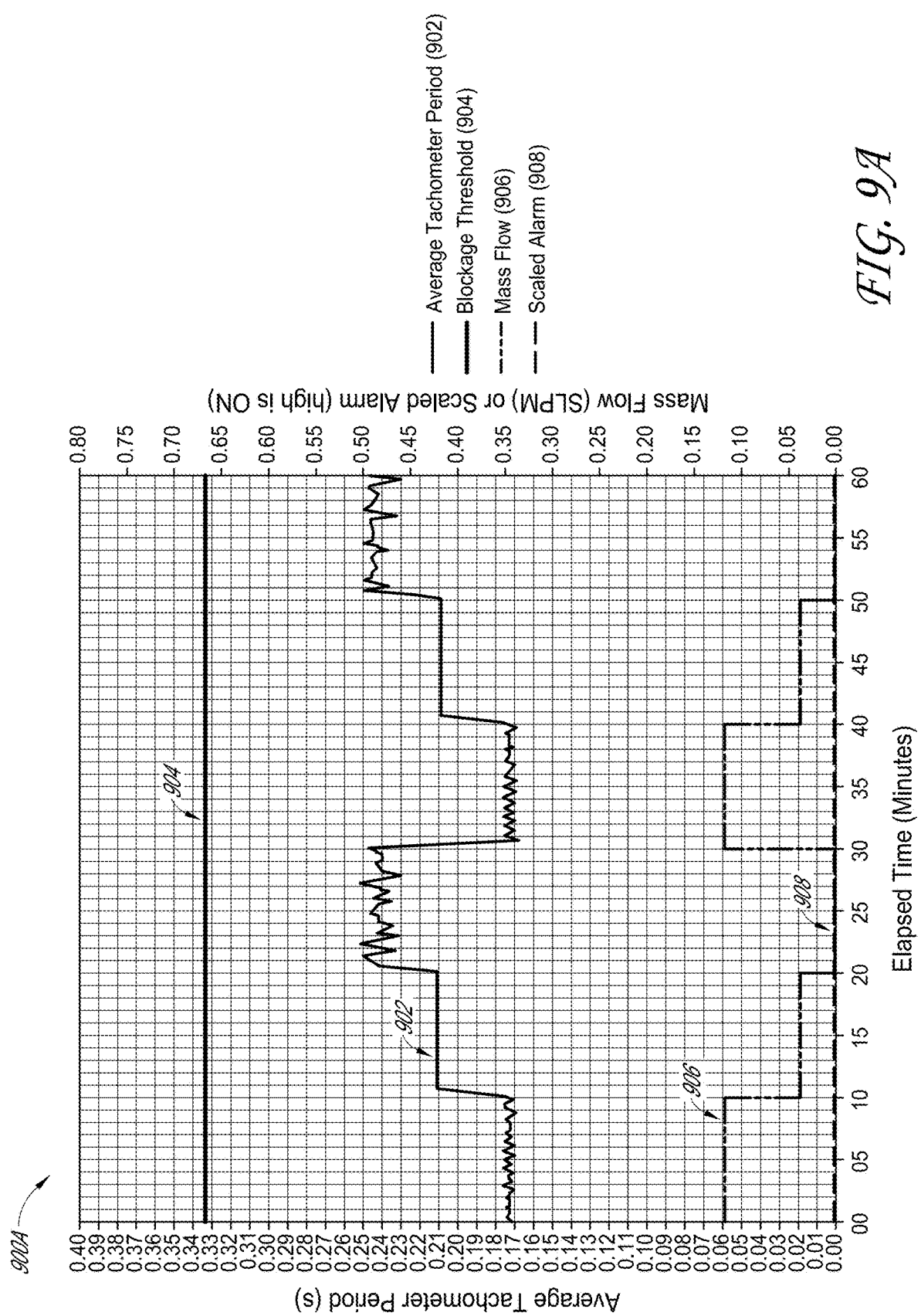

FIG. 9A shows an example plot 900A illustrating when a level of activity of a pump, such as the pump 330, may be indicative a blockage according to some embodiments, The plot 900A can be a plot for a pump assembly, such as the pump assembly 230, which includes the components 300C discussed with respect to FIG. 3C, as well as a tachometer configured to provide pulses indicative of a rotation of a pump motor of the pump. The pump assembly can be operating at a setpoint of −120 mmHg. The y-axis of the plot 900A provides an average time period between consecutive tachometer pulses in seconds (scale on the left), mass flow measure in SLIM (scale on the right), and scaled alarm indication (high corresponds to "ON"). The x-axis of the plot 900A provides elapsed time in minutes, The plot 900A depicts an average tachometer period 902, a blockage threshold setting 904, a mass flow measurement 906, and a scaled alarm 908 over time. The scaled alarm 908 can be indicative of an alarm condition, such as a blockage condition, when high. The scaled alarm 908 can, for instance, (i) be used to activate and deactivate an alarm, which can be audibly or visually perceptible, (ii) be an alarm flag in memory, or (iii) involve changing operation of the pump.

The plot 900A illustrates, for instance, how the scaled alarm 908 may not activate when the average tachometer period 902 does not satisfy the blockage threshold setting 904. As can be seen, the average tachometer period 902 remains below the blockage threshold setting 904 such that the scaled alarm 908 remains deactivated. However, the mass flow measurement 906 illustrates little to no flow in the fluid flow path, which is indicative of a blockage condition.

Figure 9B:
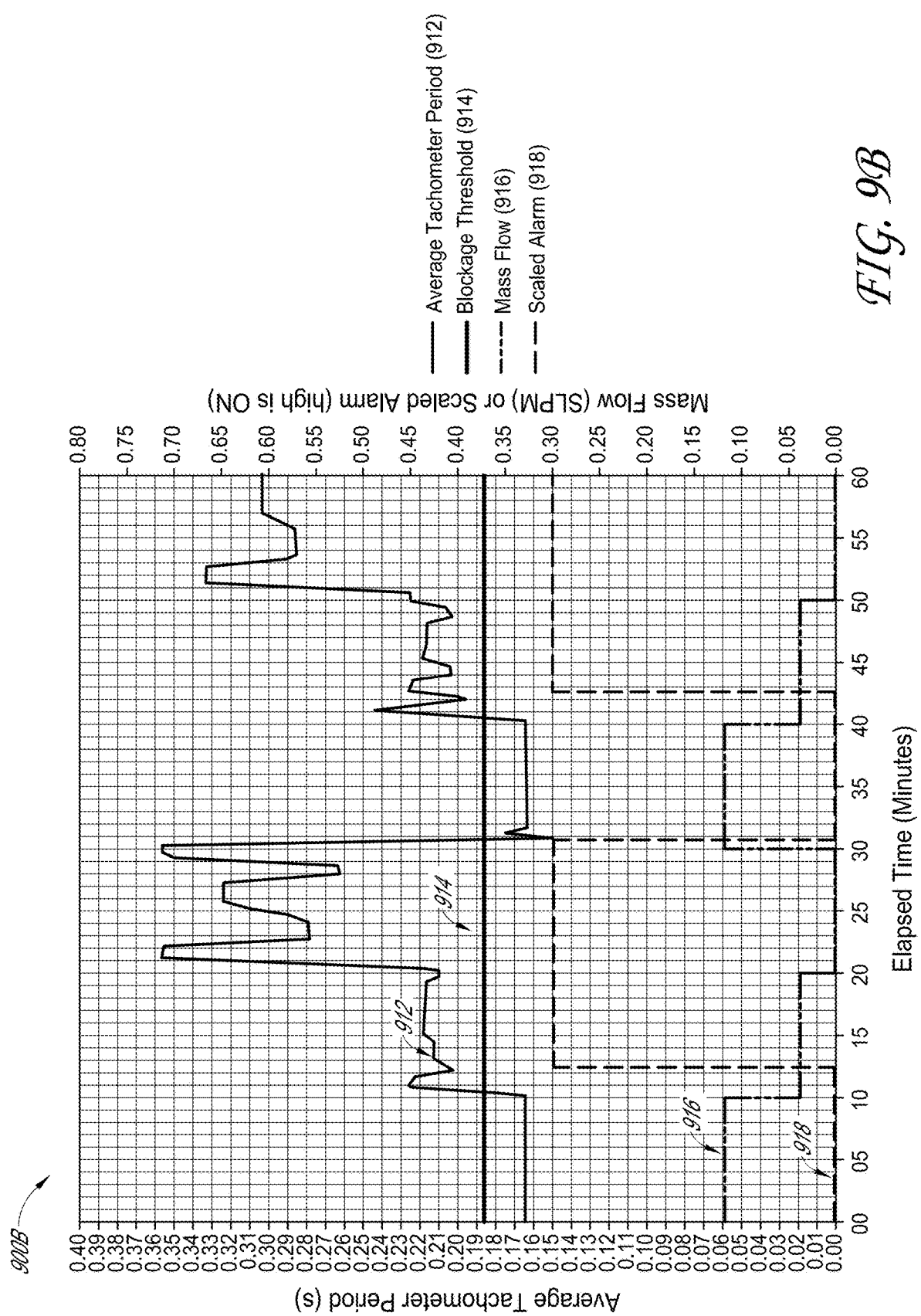

FIG. 9B shows an example plot 900B illustrating when a level of activity of a pump, such as the pump 330, may be indicative a blockage according to some embodiments. The plot 900B can be a plot for a pump assembly, such as the pump assembly 230, which includes the components 300A discussed with respect to FIG. 3A, as well as a tachometer configured to provide pulses indicative of a rotation of a pump motor of the pump. The pump assembly can be operating at a setpoint of −120 mmHg. The y-axis of the plot 900B provides an average time period between consecutive tachometer pulses in seconds (scale on the left), mass flow measure in SLPM (scale on the right), and scaled alarm indication (high corresponds to "ON") The x-axis of the plot 900B provides elapsed time in minutes. The plot 900B depicts an average tachometer period 912, a blockage threshold setting 914, a mass flow measurement 916, and a scaled alarm 918 over time. The scaled alarm 918 can be indicative of an alarm condition, such as a blockage condition, when high. The scaled alarm 918 can, for instance, (i)

be used to activate and deactivate an alarm, which can be audibly or visually perceptible, (ii) be an alarm flag in memory, or (iii) involve or trigger changing operation of the pump. In comparison with the average tachometer period 902 of FIG. 9A (which is obtained from a pump that does not include a fluid control valve), the average tachometer period 912 has larger, more accurate amplitude or dynamic range, so that accuracies of processing and detection are improved.

A clamped state threshold is not illustrated in FIG. 9B because it is set at an average tachometer period that exceeds the maximum value of 0.40 seconds on the y-axis (scale on the left). For example, in FIG. 8B the clamped state threshold setting 815 is set to about 0.825 seconds. However, in some embodiments, because the negative pressure setpoint in FIG. 9B is set to a larger value (−120 mmHg) than the setpoint in Figure SB (−40 mmHg), which causes the pump to have a higher level of activity (for example, pump motor to turn faster) to reach and maintain the lower negative pressure setpoint, the average tachometer period 912 is generally smaller than the average tachometer period 812. Accordingly, selecting a clamped state threshold for FIG. 9B to be same or similar to the clamped state threshold setting 815, which is selected for a lower negative pressure setpoint, may result in blockage detection relying only on the blockage threshold 914. The plot 900B illustrates, for instance, how the scaled alarm 918 may activate when the average tachometer period 912 satisfies the blockage threshold setting 914 instantaneously or for a period of time (for example, 10 seconds, 20 seconds, 30 seconds, 45 seconds, 1 minute, 1.5 minutes, 2 minutes, 3 minutes, etc.). As can be seen, the scaled alarm 918 can be activated at around 12 minutes and 42 minutes when the average tachometer period 912 satisfies the blockage threshold setting 914 for the period of time. The scaled alarm 918 activated at around 12 minutes and 42 minutes can thus be used to trigger a blockage threshold alarm. The scaled alarm 918 activated at around 12 minutes and 42 minutes can accordingly be deactivated at around 31 minutes when the average tachometer period 912 may no longer satisfy the blockage threshold setting 914.

By comparing the plots 800A and 800B with the plots 900A and 900B, it can be further seen that as the setpoint increases, it may be less likely for an average tachometer period to satisfy a clamped state threshold as the average tachometer period may be less likely to increase to the level of the clamped state threshold and reach saturation. In some embodiments, the clamped state threshold can be selected from a plurality of clamped state thresholds based at least on the negative pressure setpoint. For example, as the negative pressure setpoint increases, decreasing values of the clamped state threshold can be selected. Similar selection can be performed for the blockage threshold in various embodiments.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may he added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements or states. Thus, such conditional language is not generally intended to imply that features, elements or states are in any way required for one or more embodiments or that one or more embodiments necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y and Z," unless specifically stated otherwise, is to be understood with the context as used in general to convey that an item, term, etc. may be either X, Y, or Z, or a combination thereof. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. An apparatus for applying negative pressure therapy, the apparatus comprising:
    a housing comprising a source of negative pressure, the source of negative pressure including a pump configured to be in fluidic communication with a wound dressing via a fluid flow path; and
    a controller configured to operate the source of negative pressure, the controller further configured to:
    determine a level of activity of the pump,
    maintain a value in a memory responsive to the level of activity of the pump, the value being saturated when the level of activity of the pump is at or below a threshold level of activity,
    detect presence of a blockage in the fluid flow path using the level of activity of the pump and without using a pressure in the fluid flow path, and
    in response to detecting presence of the blockage in the fluid flow path, provide an indication of the blockage in the fluid flow path,
    wherein the controller is configured to detect the presence of the blockage in response to determining that the value is saturated.

2. The apparatus of claim 1, wherein the controller is configured to determine the level of activity of the pump using a signal from a tachometer, the signal being indicative of an operation of a motor of the pump.

3. The apparatus of claim 2, wherein the controller is configured to maintain the value in the memory responsive to the signal.

4. The apparatus of claim 3, wherein the controller is configured to detect the presence of the blockage in response to determining that the value is saturated for a duration of time.

5. The apparatus of claim 4, wherein the controller is configured to maintain the value in the memory by periodically adjusting the value responsive to the signal.

6. The apparatus of claim 2, wherein the tachometer is external to the pump.

7. The apparatus of claim 2, wherein the controller is configured to determine the level of activity of the pump from a duration of time between at least two consecutive pulses of the signal.

8. The apparatus of claim 7, wherein the controller is configured to detect the presence of the blockage in response to determining that the duration of time between the at least two consecutive pulses satisfies a condition indicative of a blockage.

9. The apparatus of claim 8, wherein the condition is a blockage threshold, and wherein the controller is further configured to detect the presence of the blockage in response to determining that the duration of time between the at least two consecutive pulses exceeds the blockage threshold.

10. The apparatus of claim 2, wherein the controller is configured to determine the level of activity of the pump from a duration of time between consecutive rising edges of the signal or consecutive falling edges of the signal.

11. The apparatus of claim 2, wherein the controller is configured to:
    determine durations of time between at least two pulses of the signal; and
    determine the level of activity of the pump from the determined durations of time.

12. The apparatus of claim 2, wherein the controller is configured to:
    determine a variance of time between at least three pulses of the signal; and
    determine the level of activity of the pump using the determined variance of time.

13. The apparatus of claim 2, wherein the controller is configured to determine the level of activity of the pump from a change in a period of pulses of the signal.

14. The apparatus of claim 2, wherein the controller is configured to:
    count a number of pulses of the signal for which a duration of time between consecutive pulses of the signal satisfies a condition; and
    determine the level of activity of the pump according to the count.

15. The apparatus of claim 14, wherein the condition is a threshold, and the controller is configured to count the number of pulses of the signal for which the duration of time between consecutive pulses of the signal exceeds the threshold.

16. The apparatus of claim 2, wherein the controller is configured to detect the presence of the blockage from a comparison of (1) a distribution pattern indicative of a blockage and (2) a distribution of pulses of the signal over a period of time or a number of the pulses of the signal.

17. The apparatus of claim 2, wherein the tachometer comprises a Hall effect sensor.

18. The apparatus of claim 1, wherein the controller is configured to detect the presence of the blockage in response to determining that the level of activity of the pump is indicative of an increased instability in operation of a motor of the pump.

19. The apparatus of claim 1, wherein the controller is configured to detect the level of activity without using measurements output by the pump.

20. The apparatus of claim 1, wherein the controller is configured to determine the level of activity of the pump using a signal from a tachometer internal to the pump, the signal being an encoded motor signal indicative of motion of a motor of the pump.

21. The apparatus of claim 1, wherein the controller is configured to determine the level of activity of the pump from a pulse width modulated signal used to drive a motor of the pump.

22. The apparatus of claim 1, wherein the controller is configured to detect the presence of the blockage further using a change in the level of activity of the pump.

23. The apparatus of claim 1, further comprising a flow control valve disposed between the pump and either an inlet or outlet of the housing, the flow control valve configured to permit fluid flow through the flow control valve in only one direction.

24. The apparatus of claim 1, wherein a flow control valve is not disposed between the pump and either an inlet or outlet of the housing, the flow control valve being configured to permit fluid flow through the flow control valve in only one direction.

25. The apparatus of claim 1, wherein the indication of the blockage comprises an alarm, and the controller is configured to activate the alarm in response to detecting presence of the blockage in the fluid flow path.

26. The apparatus of claim 1, further comprising a canister configured to collect fluid aspirated from under the wound dressing, wherein the blockage in the fluid flow path comprises the canister being substantially full.

* * * * *

UNITED STATES PATENT AND TRADEMARK OFFICE
CERTIFICATE OF CORRECTION

PATENT NO. : 10,549,016 B2
APPLICATION NO. : 15/540988
DATED : February 4, 2020
INVENTOR(S) : Bushko et al.

It is certified that error appears in the above-identified patent and that said Letters Patent is hereby corrected as shown below:

In the Specification

In Column 2, Line 35, delete "(n)" and insert --(ii)--.

In Column 3, Line 9, delete "sonic" and insert --some--.

In Column 5, Line 21, delete "sonic" and insert --some--.

In Column 6, Line 63, delete "system," and insert --system.--.

In Column 7, Line 5, delete "TNP)" and insert --TNP--.

In Column 8, Line 7, delete "220," and insert --220.--.

In Column 8, Line 34, delete "he" and insert --be--.

In Column 9, Line 37, delete "sonic" and insert --some--.

In Column 10, Line 23, delete "sensors," and insert --sensors.--.

In Column 10, Line 38, delete "sonic" and insert --some--.

In Column 14, Line 7, delete "Which" and insert --which--.

In Column 17, Line 59, delete "in" and insert --In--.

In Column 18, Line 21, delete "embodiments," and insert --embodiments.--.

In Column 18, Line 30, delete "SLIM" and insert --SLPM--.

Signed and Sealed this
Thirty-first Day of March, 2020

Andrei Iancu
*Director of the United States Patent and Trademark Office*

CERTIFICATE OF CORRECTION (continued)
U.S. Pat. No. 10,549,016 B2

In Column 18, Line 32, delete "minutes," and insert --minutes.--.

In Column 18, Line 61, delete ""ON")" and insert --"ON").--.

In Column 19, Line 16 (approx.), delete "SB" and insert --8B--.

In Column 20, Line 31, delete "he" and insert --be--.